(12) United States Patent
Sychev

(10) Patent No.: US 6,567,496 B1
(45) Date of Patent: May 20, 2003

(54) CARGO INSPECTION APPARATUS AND PROCESS

(76) Inventor: Boris S. Sychev, 11-84 ul. Akademika Millionschikova, 115487, Moscow (RU)

( * ) Notice: Subject to any disclaimer, the term of this patent is extended or adjusted under 35 U.S.C. 154(b) by 34 days.

(21) Appl. No.: 09/686,048

(22) Filed: Oct. 11, 2000

Related U.S. Application Data

(60) Provisional application No. 60/159,614, filed on Oct. 14, 1999.

(51) Int. Cl.⁷ .............................................. G01N 23/04
(52) U.S. Cl. .............................. 378/57; 378/88; 378/89
(58) Field of Search .......................... 378/57, 98.9, 53, 378/98.12, 90, 70, 98.11, 88, 89

(56) References Cited

U.S. PATENT DOCUMENTS

| | | |
|---|---|---|
| 5,319,547 A | 6/1994 | Krug et al. |
| 5,442,672 A | 8/1995 | Bjorkholm et al. |
| 5,490,218 A | 2/1996 | Krug et al. |
| 5,600,700 A | 2/1997 | Krug et al. |
| 5,642,393 A | 6/1997 | Krug et al. |

OTHER PUBLICATIONS

Richard F. Eilbert and Kristoph D. Kug, *Aspects of Image Recognition In Vivid Technologies Dual Energy X–ray System for Explosive Detection* SPIE vol. 1824 (1992) /127–143.

Pratt R.H., Tseng H.K., Lee C.M. *Atomic Data and Nuclear Data Tables* Aug. 1977. vol. 20, No. 2, pp. 175–209.

Richard F. Eilbert and Kristoph D. Kug, *Aspects Of Image Recognition In Vivid Technologies Dual Energy X–ray. System For Explosive Detection* SPIE vol. 1824 (1992) / 127–143.

Pratt R.H., Tseng H.K., Lee C.M. *Atomic Data and Nuclear Data Tables* Aug. 1977. vol. 20, No. 2, pp. 175–209.

*Primary Examiner*—Robert H. Kim
*Assistant Examiner*—George Wang

(57) ABSTRACT

A cargo inspection apparatus and process includes scanning containers with x-rays along two different planes. Outputs from x-ray sensors along the two different planes are collected for use in establishing the presence of contraband within the container. Using the sensor output data, images of the container are provided and suspicious areas and background areas are identified on the images. By using representative suspicious area and background area geometry and compensating in the suspicious area for the effective estimated background thereat, the average atomic number and density of the suspicious contraband is established. The average atomic number and density is then compared with known atomic numbers and densities of contraband materials and an output indicative of whether the suspicious area falls within the parameters of actual contraband material is provided.

12 Claims, 17 Drawing Sheets

$U(M_V, N_V)$ Matrix

| Detector Ordinal Number, $N_V$ | Interrogation Ordinal Number, $M_V$ | | | | |
|---|---|---|---|---|---|
| | 1 | 2 | 3 | 4 | ... |
| 1 | $U(1,1)$ | $U(2,1)$ | $U(3,1)$ | $U(4,1)$ | ... |
| 2 | $U(1,2)$ | $U(2,2)$ | $U(3,2)$ | $U(4,2)$ | ... |
| 3 | $U(1,3)$ | $U(2,3)$ | $U(3,3)$ | $U(4,3)$ | ... |
| 4 | $U(1,4)$ | $U(2,4)$ | $U(3,4)$ | $U(4,4)$ | ... |
| ... | ... | ... | ... | ... | ... |
| $N_{Vmax}$ * | $U(1, N_{Vmax})$ | $U(2, N_{Vmax})$ | $U(3, N_{Vmax})$ | $U(4, N_{Vmax})$ | ... |

\* $N_{Vmax}$ is the number of elementary detectors (sensors) in detector 8

$U(M_H, N_H)$ Matrix

| Detector Ordinal Number, $N_H$ | Interrogation Ordinal Number, $M_H$ | | | | |
|---|---|---|---|---|---|
| | 1 | 2 | 3 | 4 | ... |
| 1 | $U(1,1)$ | $U(2,1)$ | $U(3,1)$ | $U(4,1)$ | ... |
| 2 | $U(1,2)$ | $U(2,2)$ | $U(3,2)$ | $U(4,2)$ | ... |
| 3 | $U(1,3)$ | $U(2,3)$ | $U(3,3)$ | $U(4,3)$ | ... |
| 4 | $U(1,4)$ | $U(2,4)$ | $U(3,4)$ | $U(4,4)$ | ... |
| ... | ... | ... | ... | ... | ... |
| $N_{Hmax}$ * | $U(1, N_{Hmax})$ | $U(2, N_{Hmax})$ | $U(3, N_{Hmax})$ | $U(4, N_{Hmax})$ | ... |

\* $N_{Hmax}$ is the number of elementary detectors (sensors) in detector 12

Fig. 3

$U_1(M_V, N_{VO})$ Matrix
(for grid filter implementation mode)

| Detector Ordinal Number, $N_{VO}$ | Interrogation Ordinal Number, $M_V$ | | | | |
|---|---|---|---|---|---|
| | 1 | 2 | 3 | 4 | ... |
| 1 | $U_1(1,1)$ | $U_1(2,1)$ | $U_1(3,1)$ | $U_1(4,1)$ | ... |
| 3 | $U_1(1,3)$ | $U_1(2,3)$ | $U_1(3,3)$ | $U_1(4,3)$ | ... |
| 5 | $U_1(1,5)$ | $U_1(2,5)$ | $U_1(3,5)$ | $U_1(4,5)$ | ... |
| 7 | $U_1(1,7)$ | $U_1(2,7)$ | $U_1(3,7)$ | $U_1(4,7)$ | ... |
| ... | ... | ... | ... | ... | ... |
| $N_{Vmax}-1$* | $U_1(1, N_{Vmax})$ | $U_1(2, N_{Vmax})$ | $U_1(3, N_{Vmax})$ | $U_1(4, N_{Vmax})$ | ... |

* $N_{Vmax} - 1$ is the maximal odd nU1meral of elementary detector (sensor) detector 8

$U_1(M_H, N_{HO})$ Matrix
(for grid filter implementation mode)

| Detector Ordinal Number, $N_{HO}$ | Interrogation Ordinal Number, $M_H$ | | | | |
|---|---|---|---|---|---|
| | 1 | 2 | 3 | 4 | ... |
| 1 | $U_1(1,1)$ | $U_1(2,1)$ | $U_1(3,1)$ | $U_1(4,1)$ | ... |
| 3 | $U_1(1,3)$ | $U_1(2,3)$ | $U_1(3,3)$ | $U_1(4,3)$ | ... |
| 5 | $U_1(1,5)$ | $U_1(2,5)$ | $U_1(3,5)$ | $U_1(4,5)$ | ... |
| 7 | $U_1(1,7)$ | $U_1(2,7)$ | $U_1(3,7)$ | $U_1(4,7)$ | ... |
| ... | ... | ... | ... | ... | ... |
| $N_{Hmax}-1$* | $U_1(1, N_{Hmax}-1)$ | $U_1(2, N_{Hmax} - 1)$ | $U_1(3, N_{Hmax} - 1)$ | $U_1(4, N_{Hmax} - 1)$ | ... |

* $N_{Hmax} - 1$ is the maximal odd numeral of elementary detector (sensor) detector 12

Fig. 6

$U_2(M_V, N_{VE})$ Matrix
(for grid filter implementation mode)

| Detector Ordinal Number, $N_{VE}$ | Interrogation Ordinal Number, $M_V$ | | | | |
|---|---|---|---|---|---|
|  | 1 | 2 | 3 | 4 | ... |
| 2 | $U_2(1,2)$ | $U_2(2,2)$ | $U_2(3,2)$ | $U_2(4,2)$ | ... |
| 4 | $U_2(1,4)$ | $U_2(2,4)$ | $U_2(3,4)$ | $U_2(4,4)$ | ... |
| 6 | $U_2(1,6)$ | $U_2(2,6)$ | $U_2(3,6)$ | $U_2(4,6)$ | ... |
| 8 | $U_2(1,8)$ | $U_2(2,8)$ | $U_2(3,8)$ | $U_2(4,8)$ | ... |
| ... | ... | ... | ... | ... | ... |
| $N_{Vmax}$* | $U_2(1, N_{Vmax})$ | $U_2(2, N_{Vmax})$ | $U_2(3, N_{Vmax})$ | $U_2(4, N_{Vmax})$ | ... |

* $N_{Vmax}$ is the maximal even numeral of elementary detector (sensor) detector 8

$U_2(M_H, N_{HE})$ Matrix
(for grid filter implementation mode)

| Detector Ordinal Number, $N_{HE}$ | Interrogation Ordinal Number, $M_H$ | | | | |
|---|---|---|---|---|---|
|  | 1 | 2 | 3 | 4 | ... |
| 2 | $U_2(1,2)$ | $U_2(2,2)$ | $U_2(3,2)$ | $U_2(4,2)$ | ... |
| 4 | $U_2(1,4)$ | $U_2(2,4)$ | $U_2(3,4)$ | $U_2(4,4)$ | ... |
| 6 | $U_2(1,6)$ | $U_2(2,6)$ | $U_2(3,6)$ | $U_2(4,6)$ | ... |
| 8 | $U_2(1,8)$ | $U_2(2,8)$ | $U_2(3,8)$ | $U_2(4,8)$ | ... |
| ... | ... | ... | ... | ... | ... |
| $N_{Hmax}$* | $U_2(1, N_{Hmax})$ | $U_2(2, N_{Hmax})$ | $U_2(3, N_{Hmax})$ | $U_2(4, N_{Hmax})$ | ... |

* $N_{Hmax}$ is the maximal even numeral of elementary detector (sensor) detector 12

Fig. 7

$Z(M_V, K_V)$ Matrix
(for grid filter implementation mode)

| Detector Pair Ordinal Number, $K_V(N_{VO}+N_{VE})$ | Interrogation Ordinal Number, $M_V$ | | | | |
|---|---|---|---|---|---|
| | 1 | 2 | 3 | 4 | ... |
| 1(1+2) | $Z(1,1)$ | $Z(2,1)$ | $Z(3,1)$ | $Z(4,1)$ | ... |
| 2(3+4) | $Z(1,2)$ | $Z(2,2)$ | $Z(3,2)$ | $Z(4,2)$ | ... |
| 3(5+6) | $Z(1,3)$ | $Z(2,3)$ | $Z(3,3)$ | $Z(4,3)$ | ... |
| 4(7+8) | $Z(1,4)$ | $Z(2,4)$ | $Z(3,4)$ | $Z(4,4)$ | ... |
| ... | ... | ... | ... | ... | ... |
| $K_{Vmax}((N_{Vmax}-1)+N_{Vmax})^*$ | $Z(1, K_{Vmax})$ | $Z(2, K_{Vmax})$ | $Z(3, K_{Vmax})$ | $Z(4, K_{Vmax})$ | ... |

* $K_{Vmax} = K_{Vma}/2$

$Z(M_H, K_H)$ Matrix
(for grid filter implementation mode)

| Detector Ordinal Number, $K_H(N_{HO}+N_{HE})$ | Interrogation Ordinal Number, $M_H$ | | | | |
|---|---|---|---|---|---|
| | 1 | 2 | 3 | 4 | ... |
| 1(1+2) | $Z(1,1)$ | $Z(2,1)$ | $Z(3,1)$ | $Z(4,1)$ | ... |
| 2(3+4) | $Z(1,2)$ | $Z(2,2)$ | $Z(3,2)$ | $Z(4,2)$ | ... |
| 3(5+6) | $Z(1,3)$ | $Z(2,3)$ | $Z(3,3)$ | $Z(4,3)$ | ... |
| 4(7+8) | $Z(1,4)$ | $Z(2,4)$ | $Z(3,4)$ | $Z(4,4)$ | ... |
| ... | ... | ... | ... | ... | ... |
| $K_{Hmax}((N_{Hmax}-1)+N_{Hmax})^*$ | $Z(1, K_{Hmax})$ | $Z(2, K_{Hmax})$ | $Z(3, K_{Hmax})$ | $Z(4, K_{Hmax})$ | ... |

* $K_{Hmax} = N_{Hmax}/2$

Fig. 8

CARGO INSPECTION APPARATUS AND PROCESS

This application claims priority under 35 USC § 119 (e)(1) of Provisional Application No. 60/159,614 filed Oct. 14, 1999.

TECHNICAL FIELD

The present invention relates to the technical field of detecting contraband such as weapons, explosives, drugs, etc., in containers such as large cargo containers and small baggage. More particularly, the present invention is directed to an apparatus and process of non-intrusive x-ray inspection of containers through which contraband can be detected.

BACKGROUND

The transport of contraband has become and continues to be a worldwide problem. For safety, compliance of laws and other numerous reasons, it is desirable to inspect containers for establishing whether or not contraband is contained therein. Because it is impractical to open and physically inspect every container traveling through, for example, airports and harbors, it is desirable that the containers be inspected in a non-intrusive manner, that is, without opening and physically inspecting. Numerous attempts and devices have heretofor been suggested for accomplishing such non-intrusive inspections. Some such devices and/or components of such devices known to applicant are disclosed in the following references:

1. U.S. Pat. No. 5,442,672, August 1995;
2. Richard F. Eilbert and Kristoph D. Kug, SPIE Vol. 1824 (1992)/127–143;
3. U.S. Pat No. 5,319,547, June 1994;
4. U.S. Pat No. 5,490,218, February 1996;
5. U.S. Pat No. 5,600,700, February 1997;
6. U.S. Pat No. 5,642,393, June 1997;
7. Pratt R. H., Tseng H. K., Lee C. M. Atom. Data. Nucl. Data. Tables. 1977. O1. 20, No. 2.P. 175–209; and,
8. Russian Federation Patent No. 2115914, 23.04.1997.

Prior non-intrusive inspection apparatus and systems, however, are inaccurate and are thus impractical because they either are incapable of detecting contraband or can not distinguish between contraband and other materials, thereby passing over and not detecting contraband or mistaking other materials for contraband and causing false alarms.

Accordingly, a need exists for a more accurate cargo inspection apparatus and process through which contraband can more accurately be detected with minimal false alarms.

SUMMARY OF THE INVENTION

It is the principal object of the present invention to overcome the above-discussed disadvantages associated with prior cargo inspection apparatus and processes.

The present invention, in summary, is an apparatus and process through which cargo and baggage containers are scanned with x-rays along two different planes. While scanning along the first plane, a first sequence of one dimensional arrays from outputs of a plurality of x-ray sensors representative of a first x-ray intensity spectrum is obtained and a second sequence of one dimensional arrays from outputs of a plurality of x-ray sensors representative of a second x-ray intensity spectrum is also obtained. Similarly, while scanning along the second plane, a second sequence of one dimensional arrays representative of a first x-ray intensity spectrum and a second sequence of one dimensional arrays representative of a second x-ray intensity spectrum are also obtained. By using the first intensity spectrum and second intensity spectrum sequence of one dimensional arrays, atomic number sequences of one dimensional arrays are calculated for both the first and second planes. By combining at least one of the first plane first or second one dimensional arrays, a first plane image is provided. Similarly, by combing at least one of the second plane first or second sequence of one dimensional arrays, a second plane image is provided. A suspicious area and a background area are then identified in at least one of the first plane image or the second plane image. By using a representative suspicious area and representative background area geometry along with the atomic number and mass thickness values of the suspicious areas and background areas and by assuming that the effect of the background area is the same in the projection through the suspicious area, the background values are subtracted or otherwise compensated for in the suspicious area values for thereby effectively removing the background and calculating the more precise average atomic number and density of the suspicious contraband. Thereafter, the average atomic number and density of the suspicious contraband is compared with known atomic numbers and densities of actual contraband materials and a visual or audible output is provided indicative of whether the suspicious contraband falls within the parameters of actual contraband material.

Preferably, in addition to the first and second plane images, first and second plane atomic number display images are also provided for aiding in the identification of suspicious contraband. More preferably, the first and second plane atomic numbers display images provide a color display of the scanned container with the various materials corresponding to different groups of atomic numbers being displayed in different colors.

In one form thereof, the present invention is directed to a process of detecting contraband within a container. The process includes the steps of scanning the container with x-rays along a first plane and obtaining a first sequence of one dimensional arrays from outputs of a plurality of x-rays sensors representative of a first x-ray intensity spectrum. A second sequence of one dimensional arrays from outputs of a plurality of x-ray sensors representative of a second x-ray intensity spectrum is also obtained along the first plane. The container is further scanned with x-rays along a second plane and a second sequence of one dimensional arrays from outputs of a plurality of x-ray sensors representative of a first x-ray intensity spectrum is obtained. A second sequence of one dimensional arrays from outputs of a plurality of x-rays sensors representative of second x-ray intensity spectrum along the second plane is also obtained. By using the first plane first intensity spectrum and the second intensity spectrum sequence of one dimensional arrays, a first plane atomic number sequence of one dimensional arrays is calculated. By using the second plane first intensity spectrum and the second intensity spectrum sequence of one dimensional arrays, a second plane atomic number sequence of one dimensional arrays is calculated. A first plane image is then provided by combining at least one of the first plane first or second one dimensional arrays. A second plane image is also provided by combining at least one of the second plane first or second one dimensional arrays. A suspicious area and a background area are then identified in at least one of the first plane image or the second plane image. Using a representative suspicious area and background area geometry, along with the atomic number and mass thickness values of the suspicious areas and background areas, the average atomic number and density of the suspicious contraband is calculated. The average atomic number and density of the suspicious contraband are then compared with known atomic numbers and densities of actual contraband materials and an output is provided indicative or whether the suspicious contraband falls within the parameters of actual contraband material.

BRIEF DESCRIPTION OF THE DRAWINGS

The above-mentioned and other features and objects of this invention and the manner of obtaining them will become more apparent and the invention itself will be better understood by reference to the following description of the embodiments of the invention taken in conjunction with accompanying drawings wherein:

FIG. 3 is a depiction of matrices of one dimensional array outputs of the sensors along the two different planes;

FIG. 6 depicts matrices of outputs from every other sensor (odd sensors);

FIG. 7 depicts matrices of outputs from every other sensor (even sensors);

FIG. 8 depicts matrices of calculated atomic numbers along both of the planes;

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF THE PREFERRED EMBODIMENTS

Figure 1:
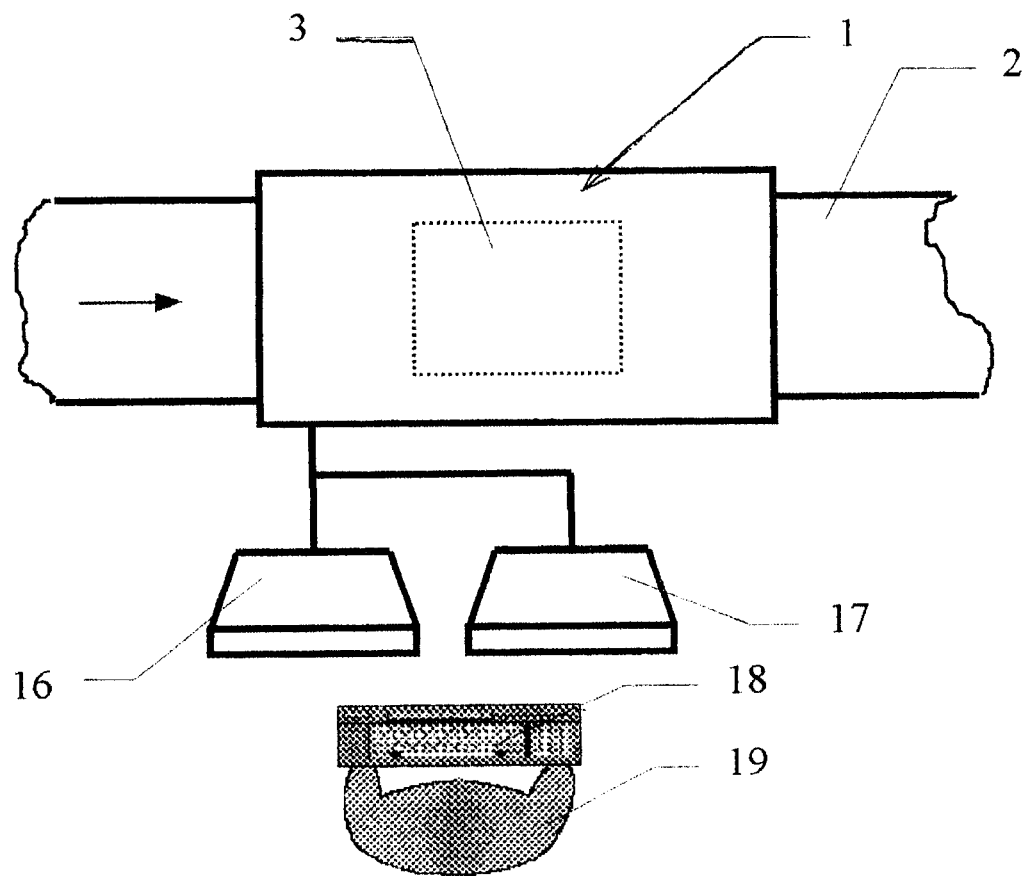
FIG. 1 is a diagrammatic plan view of a cargo inspection apparatus constructed in accordance with the principles of the present invention.
Figure 2:
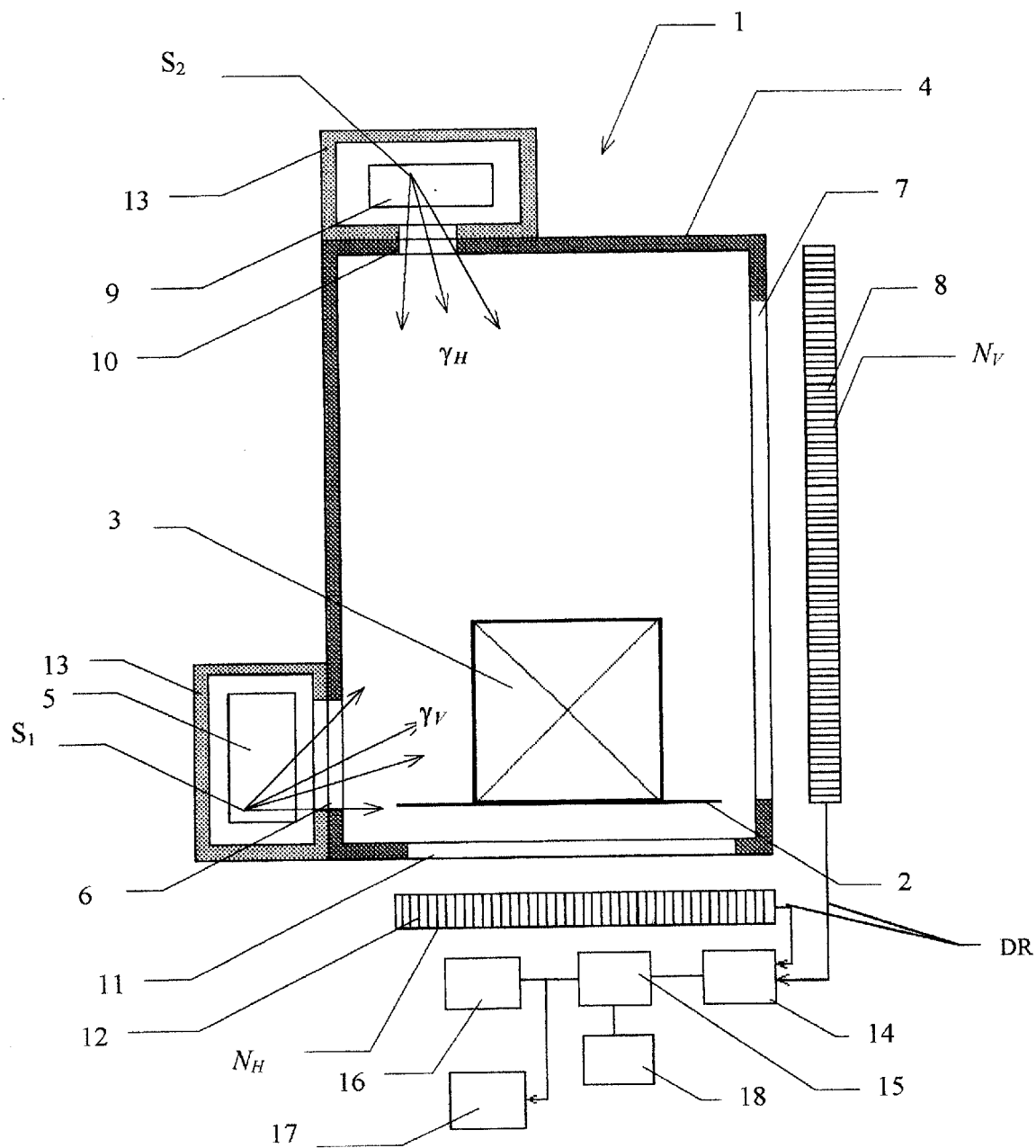
FIG. 2 is a diagrammatic sectional view of a cargo inspection apparatus constructed in accordance with the principles of the present invention, and further diagrammatically showing a container being scanned along two different planes and sensors providing outputs along the two different planes for creating sequences of one dimensional arrays which are then stored and used for computing and establishing the presence of contraband.

A cargo inspection apparatus constructed in accordance with the principles of the present invention is diagrammatically shown and generally designated by the numeral 1 in FIGS. 1 and 2.

Apparatus 1 includes a conveyor 2 for transporting cargo such as an object or package 3 in known and customary manner. Conveyor 2 extends through an inspection chamber housing 4 made of radiation shielding material such as lead. As more fully discussed hereinbelow, apparatus 1 and the process of operation thereof are provided so that the various packages and/or objects 3 may be passed through the inspection chamber housing 4 on conveyor 2 whereat they are inspected, typically for determining whether they contain contraband such as weapons, explosives, drugs, etc.

Referring more particularly to the diagrammatic cross-section of the inspection chamber 4 of FIG. 2, apparatus 1 is further provided with an x-ray source 5 with focus $S_1$ for selectively providing x-ray beam $\gamma_V$ through a window 6. As shown, the beam of x-rays $\gamma_V$ from source 5 projects or travels generally horizontally across the inspection chamber housing 4, whereat it travels through window 7 and falls on or is received by the vertical multi-channel detector 8. Multi-channel detector 8 is essentially made up of a plurality of x-ray elementary detectors (sensors) $N_V$ spaced vertically as shown and having an output for each sensor which is generally proportional to the intensity of the x-ray beam being detected. Thus, for each x-ray beam portion, each of the sensors $N_V$ provides an output which is dependent on the density and x-ray absorbing ability of the object 3 and its contents. Naturally, if no object is in the path of the x-ray beam $\gamma_V$, all of the sensors $N_V$ of detector 8 will have an output which is substantially the same. Additionally, if a very dense or highly x-ray absorbing item is within the object 3, the x-ray beam $\gamma_V$ is substantially attenuated by that item and the sensors therebehind have a proportionally lower output.

A second x-ray source 9 with focus $S_2$ is also provided and selectively provides beams of x-rays $\gamma_H$ through a window 10 generally vertically downwardly as shown. The beam $\gamma_H$ of x-rays from source 9 travels through the object 3, conveyor 2 and window 11 whereat it falls or is received and is detected by the horizontally disposed multi-channel detector 12. Multi-channel detector 12 is similarly made up of a plurality of individual x-ray elementary detectors (sensors) $N_H$ which are horizontally disposed as shown and have an output proportional to the intensity of the x-ray beam received thereat.

Each of the x-ray sources 5 and 9 are housed by, for example, shielding elements 13 to prevent radiation leakage.

The outputs of each of the sensors $N_V$ and $N_H$ of the multi-channel detectors 8 and 12 are received by analog to digital circuitry diagrammatically depicted by the numeral 14 and which converts, at any given point in time, the analog outputs from each of sensors $N_V$ and $N_H$ of detectors 8 and 12 into digital values. More specifically, at any point in time, analog to digital converter 14 converts and provides a one dimensional digital array of values for the vertically situated sensors of detector 8, and another one dimensional digital array of values for the horizontally situated sensors of detector 12.

These one dimensional digital arrays of values are processed and saved by a computer 15 for displaying images of the object on computer screens 16 and 17. A computer input device 18 such as a keyboard or a mouse is also provided and is connected to the computer 15 for use and control by the operator 19. (See FIG. 1)

Figure 4:
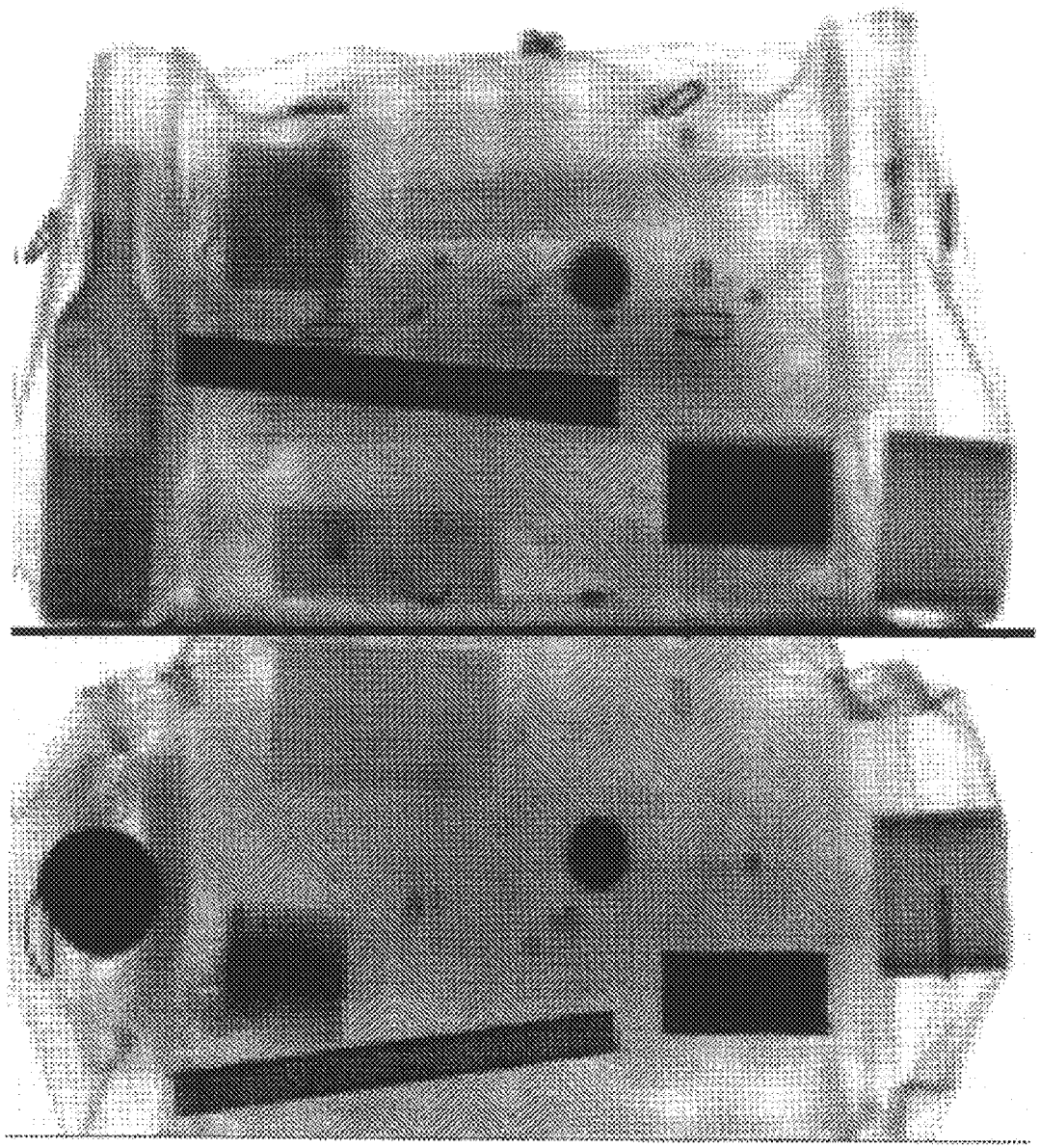
FIG. 4 is an example of gray scale x-ray images of a container and wherein each image is along a different plane.

In operation, as an object 3 is traveling through the inspection chamber 4 on conveyor 2, it is bombarded by x-ray beams $\gamma_V$ and $\gamma_H$ from both x-ray sources 5 and 9. The output signals of detectors 8 and 12 are provided at a frequency which is preselected depending on the speed at which object 3 is traveling and the desired resolution or accuracy of the apparatus. Nevertheless, for each x-ray beam or during each period, a one-dimensional digital array is created and stored by computer 15 for each detector 8 and 12. As object 3 is carried past detectors 8 and 12, a sequence of one dimensional arrays are created and stored, thus forming a signal matrix for each of the detectors 8 and 12. Each of the values in the signal matrices are converted by the computer to a matrix of signals $U(M_V, N_V)$ or $U(M_H, N_H)$ which can be displayed on a computer screen. The structure of these signal matrices and some other ones (for example, $B(M_V, N_V)$, $B(M_H, N_H)$, $X(M_V, N_V)$ $X(M_H, N_H)$, etc.) to be mentioned below is shown in FIG. 3. $M_V$ and $M_H$ are the numerals of interrogations (read-outs) of the detectors 8 and 12 respectively. The $M_V$ and $M_H$ interrogations (read-outs) apply to a particular cross sections of the object 3 by the x-ray beams $\gamma_V$ and $\gamma_H$ (see FIG. 2) while the object 3 is crossing the x-ray beam plane(s). $N_V$ and $N_H$ are the numerals of elementary detectors (sensors) in the detectors 8 and 12. Here and below the values noted by the index V apply to screening the object 3 by the x-ray beam $\gamma_V$, and the index H applies to screening the object 3 by the x-ray beam $\gamma_H$. Thus, the signal matrix $U(M_V, N_V)$ created from the vertical detector 8 is used for creating an x-ray image or view as would be seen from x-ray source 5 which is essentially a side view of object 3. This side view x-ray image is viewed by the operator on the computer screen 16 in a gray scale, and showing the more dense items within object 3 darker or more black than those items which are less dense. Similarly, the signal matrix $U(M_H, N_H)$ created from the signals from the horizontal detector 12 is used for creating an x-ray image of the contents of object 3 as seen from x-ray source 9 which is essentially a plan view thereof. Preferably, both the side and plan view images are displayed on a single computer screen, namely, screen 16. An example of these side and plan x-ray images as are seen by the operator is shown in FIG. 4.

It is known that the sensor output signals referred to as DR which are read out from the detectors 8 and 12 and consequently the signal values stored in the form of the $U(M_V, N_V)$ or $U(M_H, N_H)$ matrices are a function of the atomic number Z and mass thickness X of object 3 material along the x-ray path from the x-ray source focus $S_1$ or $S_2$ to the particular elementary detector $N_V$ or $N_H$ of multi-channel detector 8 or 12:

$$DR=f(Z, X).$$

In addition, the DR value at a given Z and X depends also on an x-ray intensity spectrum J(E) generated by the sources 5 and 9. The J(E) spectrum describes the energy distribution of x-ray quanta in the beam $\gamma_V$ or $\gamma_H$ and can be characterized by its shape and effective energy boundaries $E_{min}$ and $E_{max}$. The lower boundary $E_{min}$ is governed by material and thickness of a x-ray filter placed between the source 5 or 9 anode and the detectors 8 or 12. The higher boundary $E_{max}$ is related to the source 5 or 9 anode high voltage.

To analyze the object 3 material, the so called dual energy inspection mode is employed when two differing $J_1(E)$ and $J_2(E)$ spectra are used. As a result at same Z and X values (or at the same object cross section passing through the x-ray beam plane) two sensor response values $DR_1$ and $DR_2$ are obtained:

$$DR_1=f_1(Z, X);$$
$$DR_2=f_2(Z, X). \qquad (1)$$

Correspondingly two sets of image signal matrices are obtained:

$U_1(M_V, N_V)$ and $U_1(M_H, N_H)$ corresponding to $J_1(E)$ spectrum; and $U_2(M_V, N_V)$ and $U_2(M_H, N_H)$ corresponding to $J_2(E)$ spectrum, where the normalized signals defined as $U_1=DR_1/DR_{10}$ and $U_2=DR_2/DR_{20}$ are stored. $DR_{10}$ and $DR_{20}$ are the elementary detector $N_V$ or $N_H$ responses to $J_1(E)$ and $J_2(E)$ spectra respectively at X=0 (object 3 is absent).

There are two practical ways to implement a dual energy mode of object 3 inspection. The first is to vary the higher x-ray spectrum boundary $E_{max}$, that is to have two different anode voltages. The second is to modify the lower spectrum boundary $E_{min}$ which means to have two different x-ray filtration levels.

Figure 5:
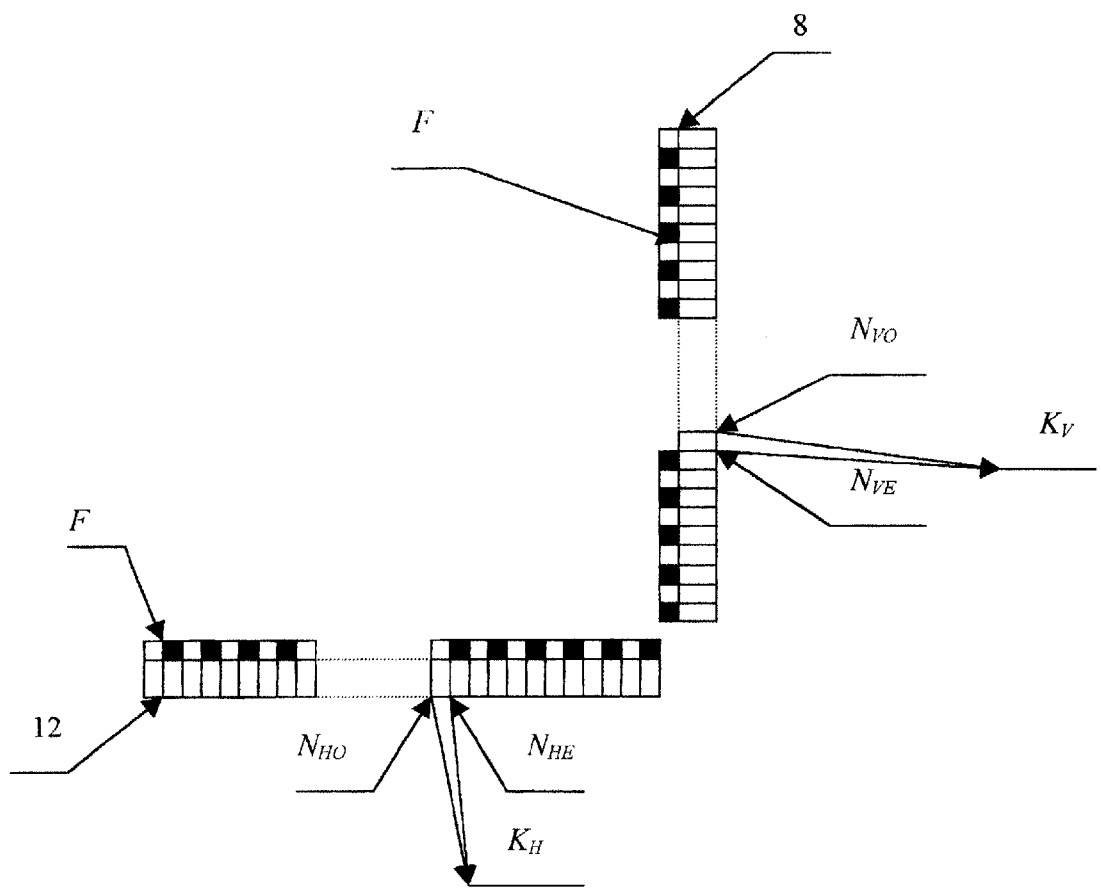
FIG. 5 is a diagrammatic view of sensors arranged along two orthogonal planes and depicting filtering of every other sensor for thereby obtaining outputs representative of two different x-ray intensity spectrums.

In the proposed radiographic apparatus 1 dual spectra mode is implemented by incorporating the grid filters F into the multi-channel detectors 8 and 12 (see FIG. 5) so that filter material overlaps every second or every other elementary detector (for example each even sensor $N_{VE}$ or $N_{HE}$). Varying filter material and thickness provides for optimal x-ray spectrum modification. Preferably, copper grid filters of filtering thickness of 1 mm are used. The elementary detectors with odd numerals $N_{VO}$ or $N_{HO}$ remain open (are not screened by the filter material).

For this specific approach the structure of the $U_1(M_V, N_{VO})$; $U_1(M_H, N_{HO})$ and $U_2(M_V, N_{VE})$ and $U_2(M_H, N_{HE})$ matrices is illustrated in FIGS. 6 and 7.

To create the black and white image of side view, the two matrices $U_1(M_V, N_{VO})$ and $U_2(M_V, N_{VE})$ are used instead of the one matrix $U(M_V, N_V)$ described above for single energy inspection mode. To transform these two matrices into one $B(M_V, N_V)$, which is displayed as gray brightness levels onto the monitor screen 16, the specially developed correlative function $h(U_1, U_2)$ is used. By analogy two matrices $U_1(M_H, N_{HO})$ and $U_2(M_H, N_{HE})$ are used to form the $B(M_H, N_H)$ matrix and the corresponding black and white image of the plan view. The resulted black and white image is the same as shown in FIG. 4.

The calculation of the Z and X values proceeds in computer 15 in parallel with preparing the black and white image.

For the system 1 the problem of determining Z and X values, which consists in solving equation system (1), is considered in general form (irrespectively of technical dual energy mode realization), with elementary detector responses $DR_1$, and $DR_2$ being described analytically. The obtained solution in the form of the analytic algorithm with a set of free parameters is based on mathematical simulation of the elementary detector response, and therefore is valid for both mentioned above methods of implementing the dual energy inspection mode. The details of the simulation procedure and the approach to using the simulation results for approximating Z and X as a function of elementary detector responses $U_1$, and $U_2$ in dual energy inspection mode are described in Appendix 1.

The particular algorithms $FZ(U_1,U_2)$ and $FX(U_1,U_2)$ with the parameters adjusted for the preferred technical implementation of the apparatus 1 is obtained and included in the system 1 software for calculating Z and X values (see Appendix 2).

Each Z or X value resulted from combined processing of signals $U_1$ and $U_2$ detected by elementary detectors $N_V$ in multi-channel detector 8 is stored in the $Z(M_V, N_V)$ or $X(M_V, N_V)$ matrix having the structure same as shown in FIG. 3. By analogy the $Z(M_H, N_H)$ and $X(M_H, N_H)$ matrices are created on the basis of processing the signals $U_1$ and $U_2$ detected by the sensors $N_H$ of multi-channel detector 12.

In the proposed technical realization of dual energy inspection mode each Z or X value resulted from combined processing of signals detected by a pair of adjacent elementary detectors $N_{VO}$ and $N_{VE}$ (one of odd numeral and one of even numeral) in multi-channel detector 8 is stored in the $Z(M_V, K_V)$ or $X(M_V, K_V)$ matrix. $K_V$ is a sensor pair ($N_{VO}$ and $N_{VE}$) numeral. The structure of these matrices is shown in FIG. 8. By analogy the $Z(M_H, K_H)$ and $X(M_H, K_H)$ matrices are created on the basis of processing the signals detected by the sensors $N_{HO}$ and $N_{HE}$ of multi-channel detector 12.

The $Z(M_V, N_V)$ and $Z(M_H, N_H)$ (or $Z(M_V, K_V)$ and $Z(M_H, K_H)$ in proposed system) matrices are converted by the computer 15 into the $C(M_V, N_V)$ and $C(M_H, N_H)$ (or $C(M_V, K_V)$ and $C(M_H, K_H)$ in the proposed system) so that to display them on the monitor screen 17 as a Z-image of side and plan views. Preferably, the effective atomic numbers recorded in the $Z(M_V, K_V)$ and $Z(M_H, K_H)$ matrices are converted in color codes and displayed on the screen 17 in accordance with the following scheme C(Z):

1. When Z is less that 8, representative of most organic substances, the screen color shown is gray;
2. When Z is 8–12, representative of most explosives and drugs, the screen color shown is red;
3. When Z is 12–16, representative of light metals such as aluminum, the screen color shown is green;
4. When Z is greater than 16, representative of most heavier metals such as iron and copper, the screen color shown is blue.

The intervals of Z may be changed and adjusted by the operator.

Figure 9:
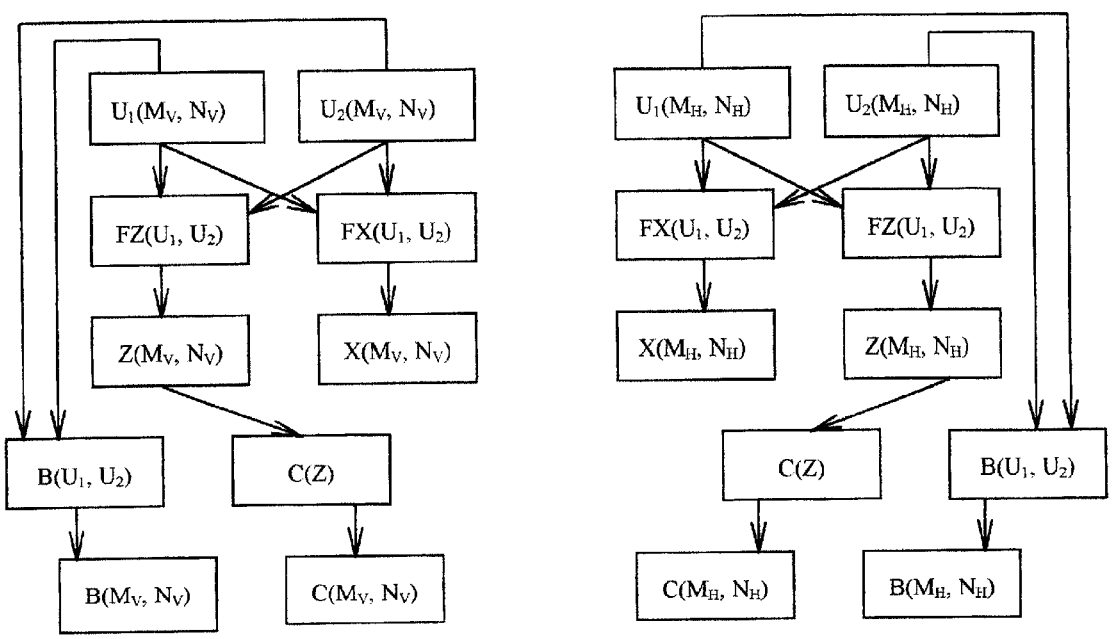
FIG. 9 is a radiographic inspection procedure flow chart.

The flowchart of the described dual energy and dual view inspection mode is presented in FIG. 9.

The Z-image displayed on the screen 17 reflects the effective atomic numbers averaged over the object 3 material along the x-ray path across the object 3 when passing from the focus $S_1$ or $S_2$ of x-ray sources 5 or 9 to the elementary detectors $N_V$ or $N_H$. Although the plan and side image views of Z-image shown on the computer screen 17 are helpful to the operator in establishing if, for example, the inspected object contains weapons, explosives or drugs, as can be appreciated, because only the effective atomic numbers of object 3 as a whole are displayed but not effective atomic numbers of items inside the object 3, it is not conclusive and can be deceiving. These images are, however, helpful to the operator in determining a potential threat.

Figure 10A:
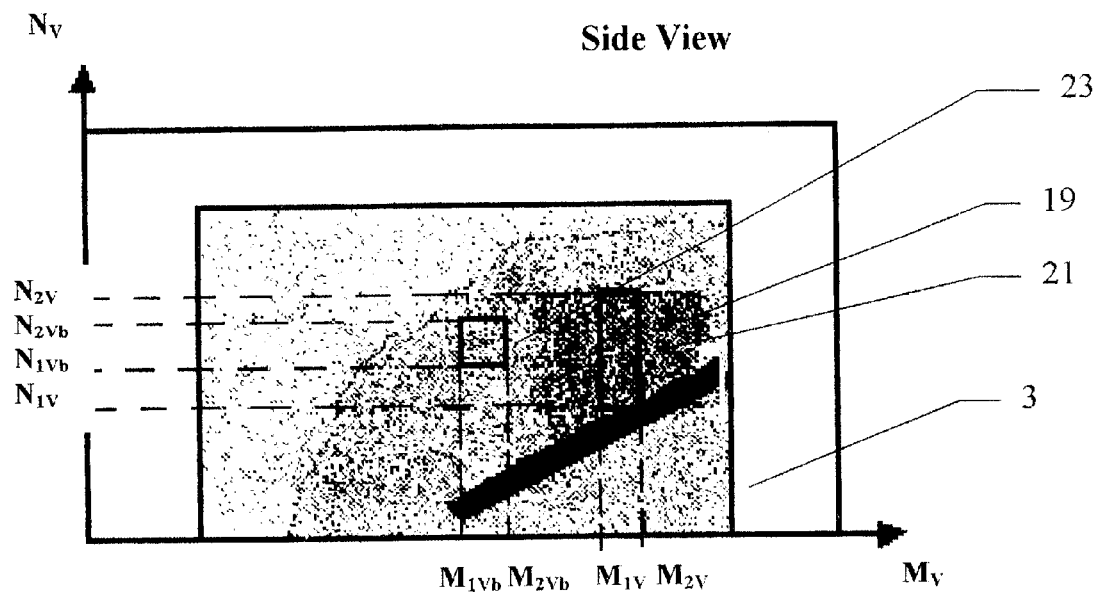
FIGS. 10a and 10b are diagrammatic views of side and plan image views of a container and depicting the identification of a suspicious area and background area and further depicting identifying by rectangle or square the representative suspicious areas and background areas for further analysis and interrogation.
Figure 10B:
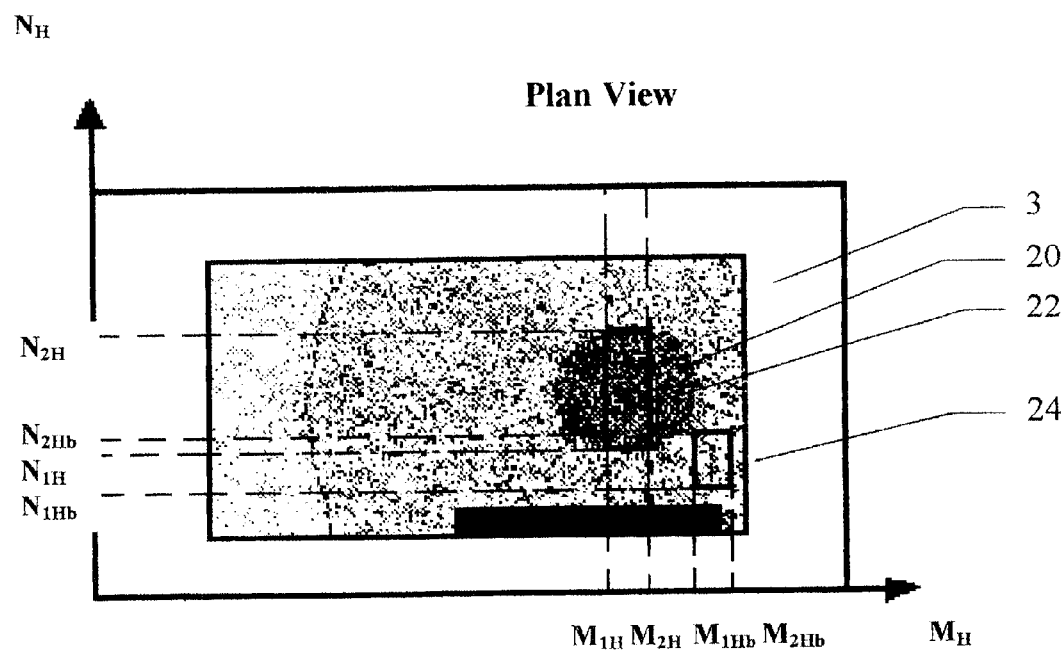
Figure 11:
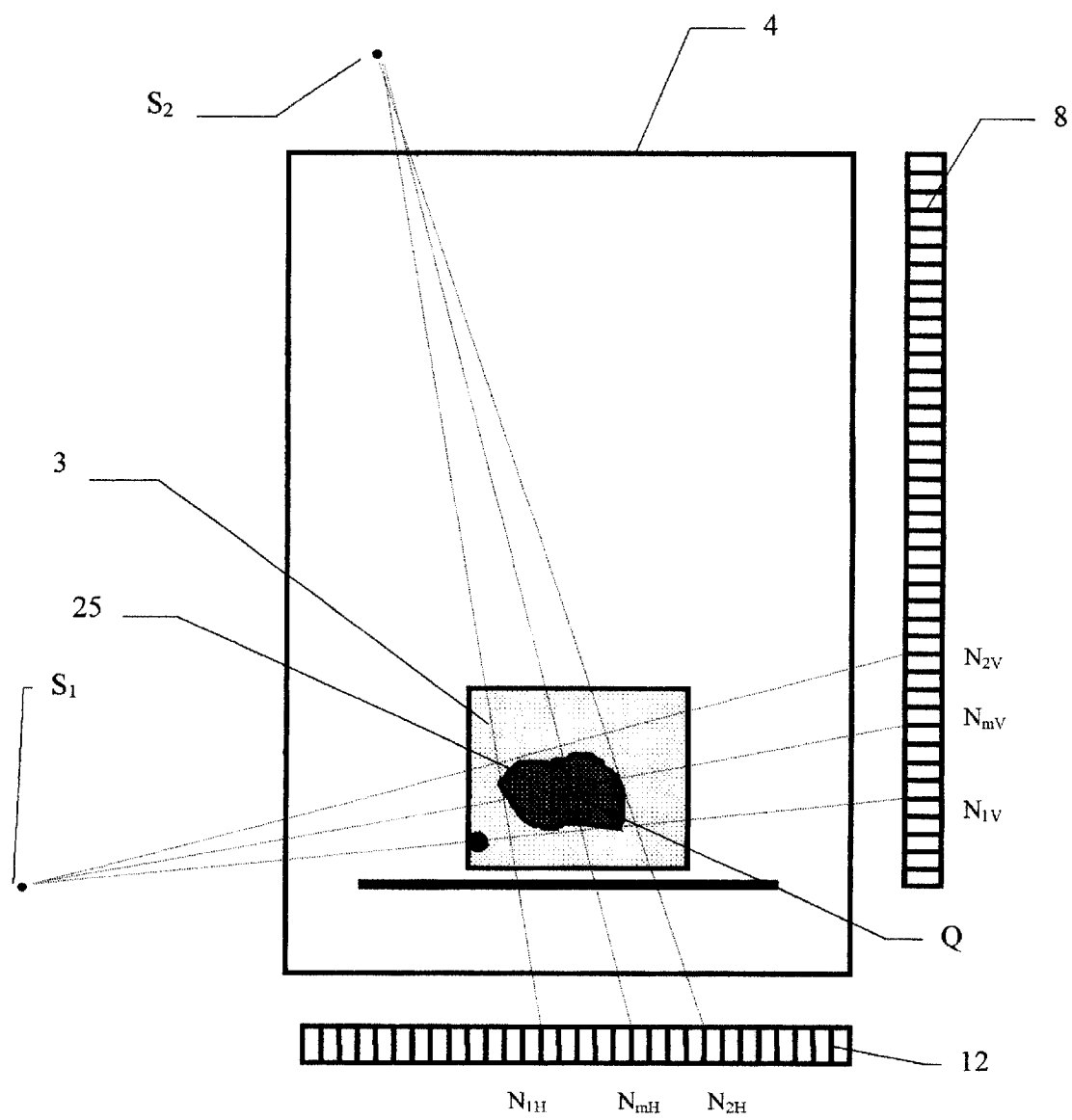
FIG. 11 is a diagrammatic side view of a cargo inspection apparatus and showing a container being scanned, and further depicting the x-ray lines of travel therethrough as ultimately would create an output by the sensors.

By viewing both computer screens 16 and 17 of the images created as described hereinabove, the operator can establish or determine suspicious or potential threatening and/or unlawful items or substances within an object 3. When a potential threat is recognized, the operator proceeds to further analyze such potential threat as described hereinbelow. In this regard, FIGS. 10a and 10b diagrammatically show x-ray black and white side and plan view images of two items inside an object 3 as are, for example, seen by the operator on computer screen 16. FIG. 11 schematically illustrates location of these items inside the object 3 applying to image shown in FIGS. 10a and 10b.

By viewing these images as well as the atomic number images thereof on screen 17 (not shown), the operator identifies the potential threat such as, for example, the darker area 19 in the side view and darker area 20 in the plan view both corresponding to item 25 (see FIG. 11). At that point, the operator, using a mouse or other computer input device 18, makes a target designation, that is points to the darker area 19 in the side view and darker area 20 in the plan view. Two implementations of target designation are realized in apparatus 1:

1. Manual Target Designation Mode

Operator draws a rectangle or square frame 21 on the suspicious area 19 in the side view of FIG. 10a and also draws a corresponding rectangle or square 22 in the suspicious or threatening area 20 of the plan view as shown in FIG. 10b.

2. Automated Target Designation Mode

Operator points or clicks with a computer mouse on the suspicious area 19 in the side view image and the rectangle frame 21 appears around the clicking point automatically. Then operator clicks on the suspicious area 20 and the rectangle frame 22 appears around the clicking point automatically. Simultaneously the background target designation proceeds in both image projections (see below).

Framing 21 initiates calculation of the average effective atomic number $Z_{Vs}$, average mass thickness $X_{Vs}$, and average geometric size (along the $\gamma_H$ beam path) $R_H$ of the framed part of object 3 as it is viewed from focus $S_1$ of the x-ray source 5. Concurrently errors $\Delta Z_{Vs}$ and $\Delta X_{Vs}$ are determined. Framed part of object 3 contains material of potential threat 25 and other materials against or in front of and behind potential threat 25 along the path of the x-ray beam $\gamma_V$ through the object 3. The matrices $Z(M_V, N_V)$ and $X(M_V, N_V)$ (or $Z(M_V, K_V)$ and $X(M_V, K_V)$ for proposed system) are used for calculation. Averaging is performed over the matrix elements which fall inside boundaries specified by the frame 21, that is, over the matrix elements with interrogation numerals $M_V$ from $M_{1V}$ to $M_{2V}$ and elementary detector numerals $N_V$ from $N_{1V}$ to $N_{2V}$ (see FIGS. 10a and 11).

Framing 22 initiates calculation of the average effective atomic number $Z_{Hs}$, average mass thickness $X_{Hs}$, and average geometric size (along the $\gamma_V$ beam path) $R_V$ of the framed part of object 3 as it is viewed from focus $S_2$ of the x-ray source 9. Concurrently errors $\Delta Z_{Hs}$ and $\Delta X_{Hs}$ are determined. Framed part of object 3 contains material of potential threat 25 and other materials against or in front of and behind potential threat 25 along the path of the x-ray beam $\gamma_H$ through the object 3. The matrices $Z(M_H, N_H)$ and $X(M_H, N_H)$ (or $Z(M_H, K_H)$ and $X(M_H, K_H)$ for proposed system) are used for calculation. Averaging is performed over the matrix elements which fall inside boundaries specified by the frame 22, that is over the matrix elements with interrogation numerals $M_H$ from $M_{1H}$ to $M_{2H}$ and elementary detector numerals $N_H$ from $N_{1H}$ to $N_{2H}$ (see FIGS. 10b and 11).

Figure 12:
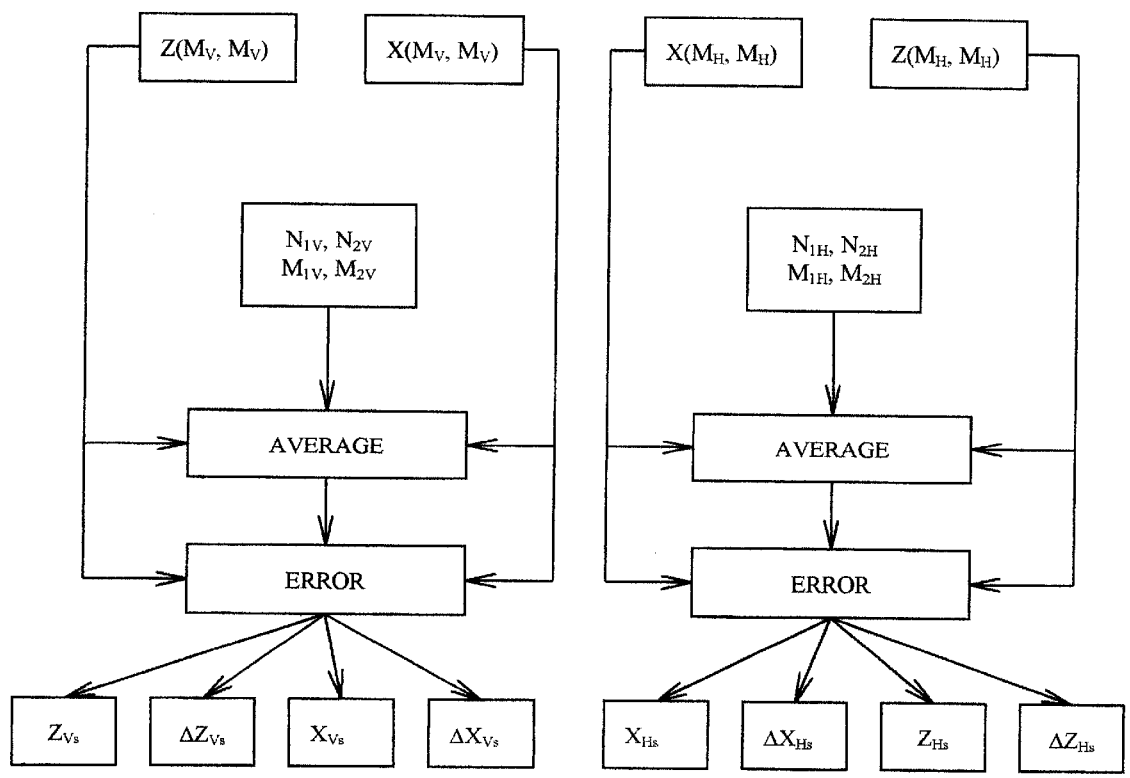
FIGS. 12–16 are flow charts depicting the inspection process in accordance with the present invention; and, FIG. 17 is a diagrammatic view depicting x-ray radiation passing through a volume containing suspicious materials.

The flowchart of calculating the average effective atomic numbers $Z_{Vs}$ and $Z_{Hs}$, average mass thicknesses $X_{Vs}$ and $X_{Hs}$ is shown in FIG. 12.

Figure 13:
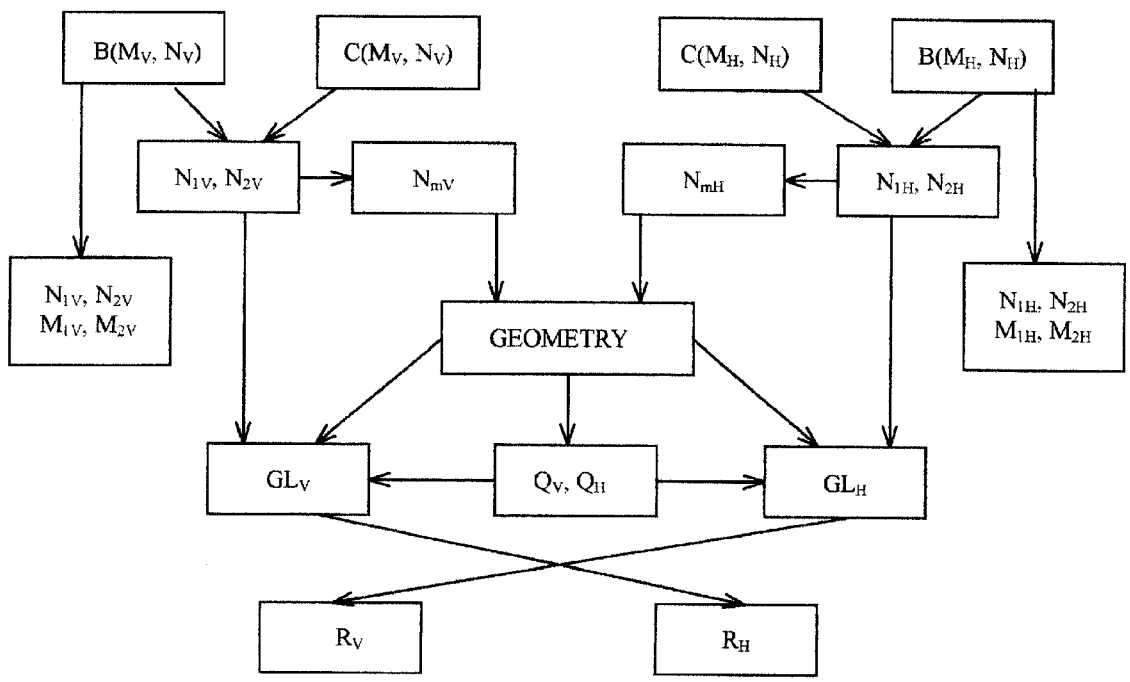

Values of $N_{1V}$, $N_{2V}$ and $N_{1H}$, $N_{2H}$ are used for determining geometrical coordinates $Q_V$, $Q_H$ of the threat object 25 center. The middle detector numerals $N_{mV}$ and $N_{mH}$ are specified (see FIG. 11). Then the specially designed software block GEOMETRY is employed, which calculates the distances from the object 25 center to the detectors 8 and 12 on the basis for the specific dimensions of the inspection chamber 4 and elementary detectors $N_V$ and $N_H$, for example in cm. After that, geometric sizes $GL_V$ and $GL_H$ of object 25 along the vertical and horizontal directions are determined in same units. Then calculating the angle of the ray from focus $S_1$ or $S_2$ to elementary detector $N_{mV}$ and $N_{mH}$ with respect to multi-channel detector 8 or 12 the geometrical size $R_H$ or $R_V$ of framed part 22 or 21 of the potential threat 25 is evaluated. The flowchart of geometrical thickness $R_H$ and $R_V$ evaluation is shown in FIG. 13.

Next is the procedure of background target designation. Also two implementations of this procedure are realized.

1. Manual Target Designation Mode

The operator, using a mouse or other computer input device 18, draws a rectangle or square 23 on the area of object 3 close to suspect area 19 in the side view of FIG. 10a. The material of object 3 corresponding to image area framed by rectangle or square 23 is considered to be equivalent to screening material against and behind potential threat 25 along the path of the x-ray beam $\gamma_V$ through the object 3. Then the operator draws a rectangle or square 24 on the area of object 3 close to suspect area 20 in the plan view of FIG. 10b. The material of object 3 corresponding to image area framed by rectangle or square 24 is considered to be equivalent to screening material against or in front of and behind potential threat 25 along the path of the x-ray beam $\gamma_H$ through the object 3. Materials of object 3 corresponding to the image areas framed by rectangles or squares 23 and 24 are called background.

2. Automated Target Designation Mode

In this case the background concept is the same as described for Manual Target Designation procedure.

Clicking on suspicious area 19 initiates the automatic analysis of the $Z(M_V, N_V)$ and $X(M_V, N_V)$ (or $Z(M_V, K_V)$ and $X(M_V, K_V)$ for proposed system) matrices according to the preset algorithm of determining background area in the side view. That is, the matrix elements, which are considered to correspond to the background material are selected. Chosen matrix elements form a set 23'. (not shown)

Clicking on suspicious area 20 initiates the automatic analysis of the $Z(M_H, N_H)$ and $X(M_H, N_H)$ (or $Z(M_V, K_H)$ and $X(M_V, K_H)$ for proposed system) matrices according to the preset algorithm of determining background area in the plan view. That is, the matrix elements, which are considered to correspond to the background material are selected. Chosen matrix elements form a set 24'. (not shown)

Drawing frame 23 or specifying set 23' initiates calculation of the average effective atomic number $Z_{Vb}$ and average mass thickness $X_{Vb}$ of the background material. Concurrently errors $\Delta Z_{Vb}$ and $\Delta X_{Vb}$ are determined. The matrices $Z(M_V, N_V)$ and $X(M_V, N_V)$ (or $Z(M_V, K_V)$ and $X(M_V, K_V)$ for proposed system) are used for calculation. Averaging is performed over the matrix elements which fall inside boundaries specified by the frame 23 or belong to set 23'. FIG. 10a illustrates the Manual Target Designation Mode when averaging is carried out over the matrix elements with interrogation numerals $M_V$ from $M_{1Vb}$ to $M_{2Vb}$ and elementary detector numerals $N_V$ from $N_{1Vb}$ to $N_{2Vb}$.

Drawing frame 24 or specifying set 24' initiates calculation of the average effective atomic number $Z_{hb}$ and average mass thickness $X_{Hb}$ of the background material. Concurrently errors $\Delta Z_{Hb}$ and $\Delta X_{Hb}$ are determined. The matrices $Z(M_H, N_H)$ and $X(M_H, N_H)$ (or $Z(M_H, K_H)$ and $X(M_H, K_H)$ for proposed system) are used for calculation. Averaging is performed over the matrix elements which fall inside boundaries specified by the frame 24 or belong to set 24'. FIG. 10b illustrates the Manual Target Designation Mode when averaging is carried out over the matrix elements with interrogation numerals $M_H$ from $M_{1Hb}$ to $M_{2Hb}$ and elementary detector numerals $N_H$ from $N_{1Hb}$ to $N_{2Hb}$.

Figure 14:
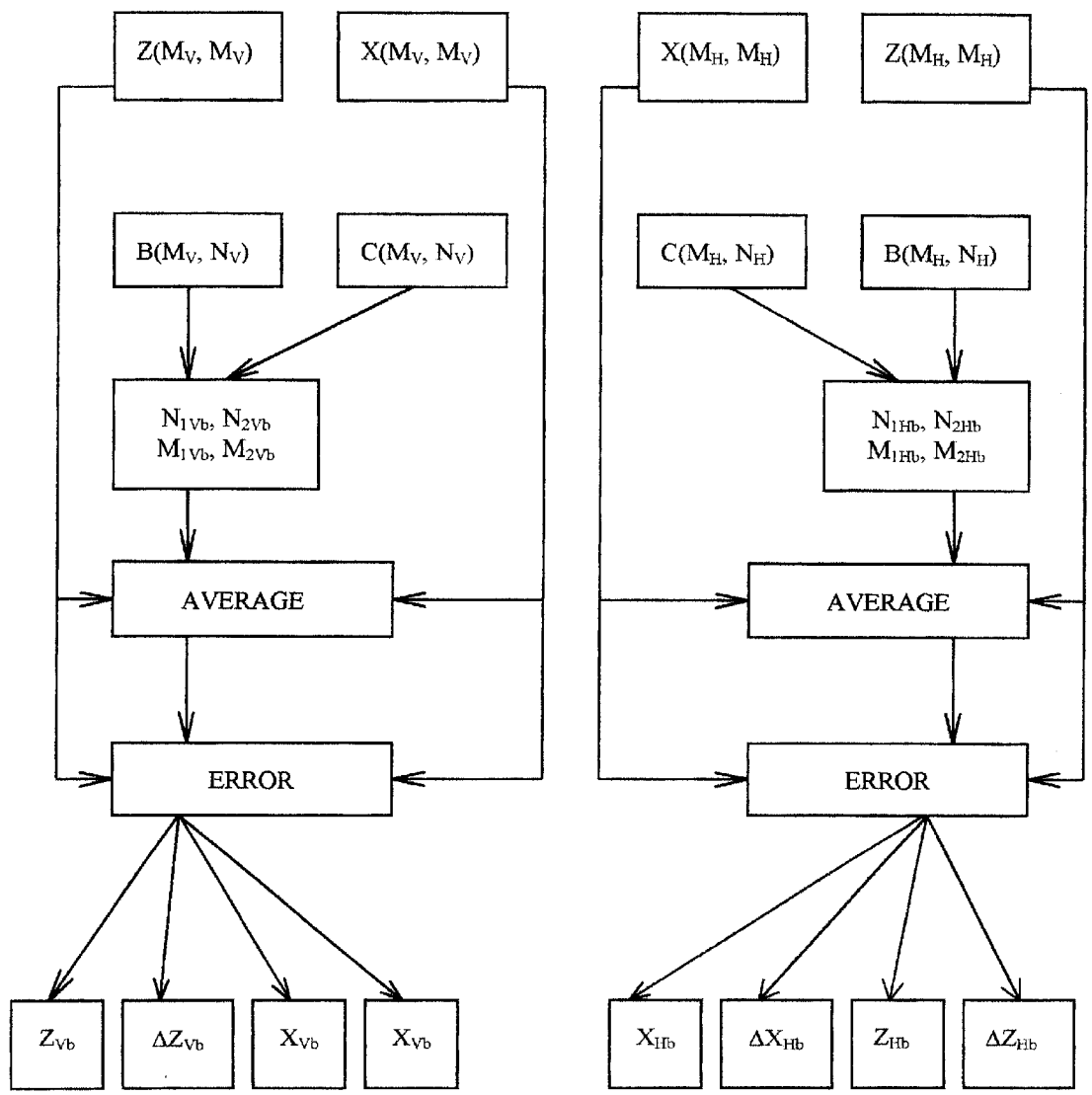

The flowchart of calculating the average effective atomic numbers $Z_{Vb}$ and $Z_{Hb}$, average mass thicknesses $X_{Vb}$ and $X_{Hb}$ of threat object 25 background is shown in FIG. 14 for Manual Target Designation Mode.

The average mass thickness $X_{Vi}$ of the potential threat 25 in side view is calculated:

$$X_{Vi} = X_{Vs} - X_{Vb}.$$

The average mass thickness $X_{Hi}$ of the potential threat 25 in plan view is calculated:

$$X_{Hi} = X_{Hs} - X_{hb}.$$

Concurrently the mass thickness errors $\Delta X_{Vi}$ and $\Delta X_{Hi}$ are determined.

The average effective atomic number of the potential threat 25 is calculated on the basis of side view data processing:

$$Z_{Vi} = \{[(Z_{vs})^a X_{Vs} - (Z_{Vb})^c X_{Vb}]/(X_{Vs} - X_{Vb})\}^{1/a}.$$

The average effective atomic number of the potential threat 25 is calculated on the basis of plan view data processing:

$$Z_{Hi} = \{[(Z_{Hs})^a X_{Hs} - (Z_{Hb})^c X_{Hb}](X_{Hs} - X_{Hb})\}^{1/a}.$$

Free parameters a and c are adjusted for the proposed technical realization of system 1.

Concurrently the average atomic number errors $\Delta Z_{Vi}$ and $\Delta Z_{Hi}$ are determined.

The concept of background subtracting procedure is described in Appendix 3.

The average atomic number $Z_i$ of potential threat 25 is calculated as a weighted average of $Z_{iV}$ and $Z_{Hi}$. Weighting factors are assigned according to $\Delta Z_{Vi}$ and $\Delta Z_{Hi}$ values.

The densities $D_{Vi}$ and $D_{Hi}$ of potential threat 25 material are calculated as follows:

$$D_{Vi} = X_{Vi}/R_{Vi.}$$

$$D_{Hi} = X_{Hi}/R_{Hi.}$$

Simultaneously the density errors $\Delta D_{Vi}$ and $\Delta D_{Hi}$ are determined.

The density $D_i$ of potential threat 25 is calculated as a weighted average of $D_{iV}$ and $D_{iH}$. Weighting factors are assigned according to $\Delta D_{Vi}$ and $\Delta D_{Hi}$ values.

Figure 15:
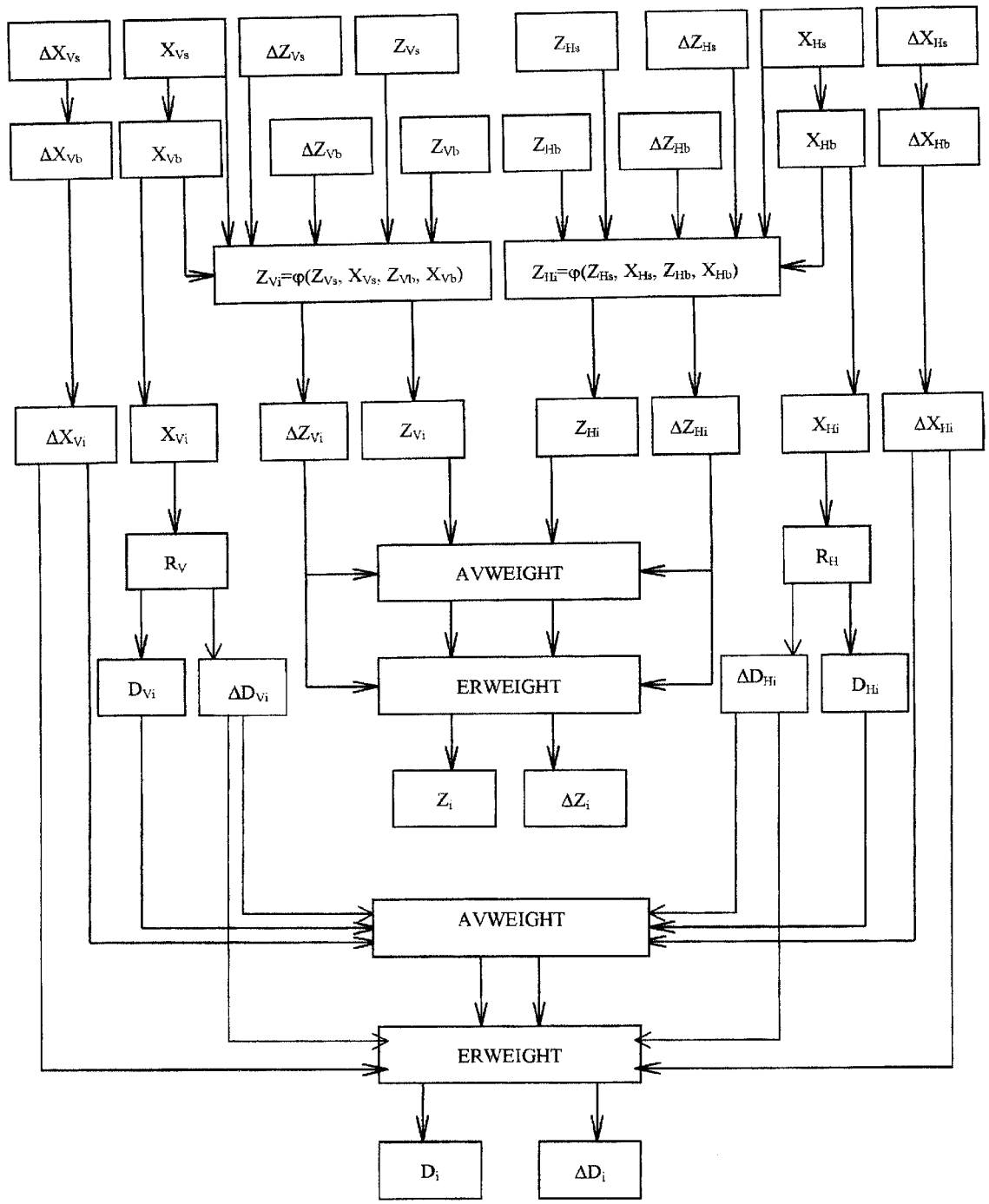

The flowchart of calculation of the average atomic number $Z_i \pm \Delta Z_i$ and average density $D_i \pm \Delta D_i$ of the threat object 25 is shown in FIG. 15.

The last step of potential threat analysis is to compare the obtained physical parameters (effective atomic number and density) of the potential threat object 25 with the physical parameters known for real threats (explosives, drugs, etc.). As a result of this comparison the decision is made whether the object 25 belongs to the particular preset group of threat materials or not.

Preferably, the several ranges of physical parameters (Z and D) characteristic for threat materials are preset and stored in the computer 15 memory in the form of data file BANK. Each range corresponds to particular interval ($Z_1$, $Z_2$) of Z and/or particular interval ($D_1$, $D_2$) of D values. The threat parameter ranges and boundaries $Z_1$ and $Z_2$; $D_1$ and $D_2$ of the corresponding Z and D intervals were predetermined according to the results of testing a great number of real threat materials and objects. The tests were carried out with the use of proposed radiographic system and can be considered as the system calibration.

Numerical values of $Z_i \pm \Delta Z_i$ and $D_i \pm \Delta D_i$ are displayed on the left monitor screen 16 under the inspected object image.

Figure 16:
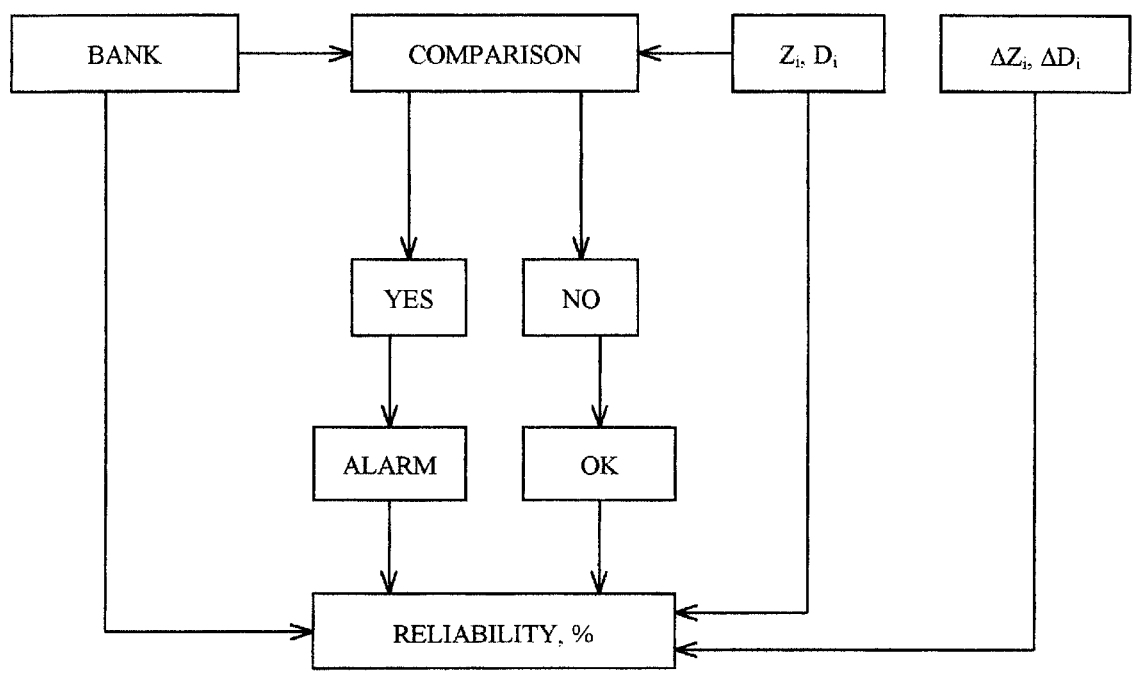

If the calculated Z and D values fall within one of the threat group ranges (a specific couple of Z and D intervals); that is if Z belongs to the preset $(Z_1, Z_2)$ interval and simultaneously D belongs to the corresponding $(D_1, D_2)$ interval, then the prompt appears on the monitor screen 16 and the alarm signal is generated by the computer 15. The displayed prompt includes the estimated value of alarm signal reliability in percents. The reliability percentage is evaluated on the basis of comparing the $\pm\Delta Z_i$ and $\pm\Delta D_i$ intervals with the corresponding $(Z_1, Z_2)$ and $(D_1, D_2)$ intervals. The flowchart of the alarm signal generation and evaluation of alarm signal reliability is shown in FIG. 16.

The proposed inspection procedure can be implemented in any dual-energy dual-projection x-ray system independent of:

1. X-ray source operation time mode (pulse or continuous).
2. Maximal energy(ies) of the used x-ray radiation spectrum (spectra).
3. Method of technical implementation of dual energy inspection mode.

In the particular case of dual projection single-energy apparatus, the function of determining the average density of the suspicious volume 25 inside the inspected baggage 3 can be implemented without Z-analysis.

In particular case of single projection dual-energy apparatus the functions of determining the average effective number $Z_i$ and average mass thickness $X_i$ of suspicious volume 25 inside the baggage 3 can be used without density analysis. This inspection mode is also available in the proposed apparatus 1 and is recommended when multiple objects overlap one another in the inspected baggage 3 or the mass thickness values of the suspected volume 25 are extreme in one of projections (for example, in plan view). In such case the average effective atomic number $Z_{Vi}$ and the average mass thickness $X_{Vi}$ of the said volume are determined in the other projection (for example, in side view).

APPENDIX 1

In the described system 1 analytical approximation process to solve the problem of restoration of effective atomic number of the x-ray absorber during inspection using different energy radiation spectra is used.

The direct problem of mathematical simulation of elementary detector response is formulated as follows:

$$DR_1 = k \int_{E_{min1}}^{E_{max1}} J_1(E)\eta(E) \exp\left(-\int_0^X \mu(E, Z(x))dx\right) dE, \quad (A1.1)$$

here $DR_1$ is the response of elementary detector (sensor) $N_V$ or $N_H$ of detectors 8 or 12;

k—proportionality factor;

$J_1(E)$ is the energy spectrum of x-ray intensity;

E is the x-ray quantum energy;

x is the integration variable in mass thickness of the inspected object along the beam passing through focus $S_1$ of the x-ray source and the elementary detector;

Z(x) is the inspected object 3 material atomic number at the point "x";

$\mu(E, Z(x))$ is the absorption mass factor of x-ray quanta having energy E by the material having atomic number Z(x);

X is the cumulative mass thickness of the inspected object 3 along the penetrating beam;

$\eta(E)$ is the efficiency of x-ray detection by sensors $N_V$ or $N_H$ of detectors 8 or 12;

In the expression (A1.1) it is assumed that $J_1(E)=0$ if $E<E_{min1}$ or $E>E_{max1}$.

If the entire layer having thickness X is assigned an effective atomic number Z such that $$\int_0^X \mu(E, Z(x))dx = \mu(E, Z)X, \quad (A1.2)$$

then expression (A2.1) can be transformed in the following manner $$DR_1(Z, X) = k \int_{E_{min1}}^{E_{max1}} J_1(E)\eta(E) \exp(-\mu(E, Z)X) dE. \quad (A1.3)$$

If inspection is performed in the spectral mode different to the initial spectral mode, i.e. if instead of spectrum $J_1(E)$ another spectrum $J_2(E)$ is used having different effective boundaries $E_{min2}$ and $E_{max2}$, then the corresponding detector response by analogy to expression (A1.3) will be presented by the following expression:

$$DR_2(Z, X) = k \int_{E_{min2}}^{E_{max2}} J_2(E)\eta(E) \exp(-\mu(E, Z)X) dE. \quad (A1.4)$$

When practically building and processing x-ray images it is feasible to use normalized values of detector responses $U_1(Z, X)$ and $U_2(Z, X)$ such that:

$$U_1(Z, X) = DR_1(Z, X)/DR_{10}, \quad (A1.5)$$

$$U_2(Z, X) = DR_2(Z, X)/DR_{20}, \quad (A1.6)$$

where $$DR_{10} = k \int_{E_{min1}}^{E_{max1}} J_1(E)\eta(E) dE, \quad (A1.7)$$

$$DR_{20} = k \int_{E_{min2}}^{E_{max2}} J_2(E)\eta(E) dE. \quad (A1.8)$$

From expressions (A1.5) and (A1.6) follows that $U_1(Z, X) \leq 1$ and $U_2(Z, X) \leq 1$. At $X=0$ $U_1$ and $U_2$ are equal to 1.

There are two practical technical solutions for dual energy x-ray inspection mode: variation of the upper spectrum boundary, i.e. performance at two different x-ray tube anode voltages, and variation of the lower spectrum boundary, i.e. performance at two different x-ray radiation filtration levels. Using expressions (A1.5) and (A1.6) and data on initial x-ray spectra [7] a direct mathematical simulation in a wide range of Z, X, and E values, which is typical for x-ray inspection was performed. It is convenient to present simulation results in terms of:

$$gg_1(Z, X) = ln(1/U_1(Z, X)), \quad (A1.9)$$

$$gg_2(Z, X) = ln(1/U_2(Z, X)), \quad (A1.10)$$

$$gg_1(Z, X) > gg_2(Z, X), \text{ if } X > 0 \quad (A1.1)$$

$$cfg(Z, X) = gg_1(Z, X)/gg_2(Z, X) - 1, \text{ or} \quad (A1.12)$$

$$cfg(Z, X) = (U_2(Z, X)/U_1(Z, X) - 1)/gg_2(Z, X). \quad (A1.12')$$

If only such materials, for which K-boundary of x-ray absorption is less than minimal meaningful energy in the spectrum, i.e. $E_K<E_{min1}$ and $E_K<E_{min2}$ are considered, then from the obtained results it follows that for any set of $gg_1$ or $gg_2$ values there exists a simple monotonous function cfg (Z). This proves the existence of inverse function $Z(gg_1, gg_2)$ where $gg_1$ and $gg_2$ are related to the responses $U_1$ and $U_2$ obtained in detector interrogations.

The mentioned inverse dependency can be expressed in the form of analytical approximation with acceptable accuracy.

APPENDIX 2

Specifically, for the proposed device 1 with additional x-ray radiation filtration implemented as grid-like filters F (see FIG. 5) following inverse dependency, i.e. algorithm establishing relationship between the value of effective atomic number Z and signal values $U_1$ and $U_2$ has been selected:

$$cfex=U_2/U1-1.$$

$$gg2=alog(1./U2)$$

$$cfg=cfex/gg2$$

$$act1=(0.83/gg2)0.363/(1.+(gg2/6.)1.5)$$

$$act2=0.5/(1.+(gg2/2.4)**0.75)$$

$$atu2=0.4+0.17*gg2**0.84$$

$$afi1=(cfg/act1)**4$$

$$afi2=(cfg/act2)**atu2$$

$$tat1=11.$$

$$tat2=9.7$$

$$hkf=0.74$$

$$fuf=cfex2/(1.+(gg2/6.)4)$$

$$hah11=tat1*afi1*hkf*(1.+fuf*hkg)$$

$$hah2=tat2*afi2$$

$$hhaa=hah2+hah11$$

$$trt=(hhaa/14.)**4$$

$$ffrr=2.4*trt/(1.+trt**2)$$

$$hah1=hah11/(1.+ffrr)$$

$$Z=hah1+hah2 \quad (A2.1)$$

Algorithm (A2.1) is notified $FZ(U_1,U_2)$ on FIG. 9.

It is convenient to present the analytical dependency of mass thickness X on signal $U_1$ and $U_2$ values in the form of function of two arguments: $gg_2$ and Z, the value of which has been determined in the previous step:

$$rr1=0.15+(1.+5.3*(Z/13.)**3.6)/100.$$

$$rd1=1./rr1$$

$$rqq3=(13.1/Z)**8$$

$$rd2=0.07+0.43/(1.+rqq3)$$

$$X=gg2*(rd1+rd2*sqrt(gg2)) \quad (A2.2)$$

Algorithm (A2.2) is notified $FX(U_1,U_2)$ on FIG. 9.

When selecting parameters for X approximation (algorithm (A2.2)) it was assumed that ratio Z/A, where A is the atomic weight, for pure substances (elements) is a monotonous function of atomic number. Analysis shows that the error, which is introduced by deviation of ratio Z/A from monotonous dependency for all real materials (with the exception of hydrogen) does not exceed several per cent.

The free parameters of presented algorithms (A2.1) and (A2.2) were adjusted for the following conditions:

1. The x-ray $J_1(E)$ spectrum is generated in the tungsten anode of the x-ray tube and filtered by layers of tungsten having 0.01 mm thickness and aluminum having thickness of 2 mm and thus generating spectrum (see expression 3).
2. Spectrum $J_2(E)$ is formed when x-rays with $J_1(E)$ spectrum pass through a 1 mm thick copper filter.
3. X-ray radiation detection effectiveness is assumed to be $\eta(E)=1$.
4. Maximal energy of both x-ray spectra $J_2(E)$ and $J_1(E)$ is the same and $E_{max1}=E_{max2}=130$ keV.

In the presented above algorithms (A2.1) and (A2.2) notation of variables typical for programming languages and mathematical operations is used.

Some results of mathematical simulation of the $gg_1$, $gg_2$, and cfg functions related to detector responses $U_1$ and $U_2$ are shown in Tables 1–3. The corresponding Z and X values restored according to algorithms (A2.1) and (A2.2) are also presented. Results for carbon absorber are in Table 1, for aluminum absorber, in Table 2, and for iron absorber, in Table 3. In these tables the following notations are used:

$Z^{(1)}$ is the real absorber material atomic number;

$X^{(1)}$ is the real absorber material mass thickness;

Z is the restored absorber material atomic number determined by signal $U_1$ and $U_2$ values;

X is the absorber mass thickness determined by values of $gg_2$ and Z.

TABLE 1

Results of mathematical simulation for carbon absorber ($Z^{(1)}$ = 6)

| $X^{(1)}$, g/cm² | $gg_1$ | $gg_2$ | Cfg | Z | $X/X^{(1)}$ |
|---|---|---|---|---|---|
| 0.42 | 0.078 | 0.068 | 0.1527 | 6.076 | 0.992 |
| 0.84 | 0.156 | 0.136 | 0.1516 | 6.075 | 0.993 |
| 1.68 | 0.311 | 0.271 | 0.1495 | 6.063 | 0.994 |
| 3.36 | 0.618 | 0.542 | 0.1457 | 6.027 | 0.996 |
| 6.30 | 1.148 | 1.015 | 0.1399 | 5.963 | 0.999 |
| 8.40 | 1.521 | 1.352 | 0.1362 | 5.921 | 1.000 |
| 12.60 | 2.258 | 2.025 | 0.1297 | 5.852 | 1.002 |
| 21.00 | 3.699 | 3.363 | 0.1189 | 5.764 | 1.004 |
| 29.40 | 5.109 | 4.692 | 0.1102 | 5.740 | 1.005 |
| 37.80 | 6.496 | 6.014 | 0.1028 | 5.792 | 1.004 |

TABLE 2

Results of mathematical simulation for aluminum absorber ($Z^{(1)}$ = 13)

| $X^{(1)}$, g/cm² | $gg_1$ | $gg_2$ | Cfg | Z | $X/X^{(1)}$ |
|---|---|---|---|---|---|
| 0.37 | 0.147 | 0.078 | 0.9120 | 12.97 | 1.013 |
| 0.74 | 0.279 | 0.156 | 0.8376 | 12.97 | 1.016 |
| 1.48 | 0.515 | 0.310 | 0.7333 | 12.97 | 1.019 |
| 2.96 | 0.930 | 0.614 | 0.6060 | 12.95 | 1.021 |
| 5.55 | 1.566 | 1.131 | 0.4824 | 12.94 | 1.020 |

TABLE 2-continued

Results of mathematical simulation for aluminum absorber ($Z^{(1)} = 13$)

| $X^{(1)}$, g/cm² | gg₁ | gg₂ | Cfg | Z | X/X^(1) |
|---|---|---|---|---|---|
| 7.40 | 1.984 | 1.492 | 0.4265 | 12.94 | 1.018 |
| 11.10 | 2.768 | 2.196 | 0.3514 | 12.96 | 1.013 |
| 18.50 | 4.223 | 3.558 | 0.2656 | 13.04 | 1.002 |
| 25.90 | 5.594 | 4.875 | 0.2157 | 13.09 | 0.996 |
| 33.30 | 6.917 | 6.161 | 0.1832 | 13.21 | 0.990 |

TABLE 3

Results of mathematical simulation for iron absorber ($Z^{(1)} = 26$)

| $X^{(1)}$, g/cm² | gg₁ | gg₂ | Cfg | Z | X/X^(1) |
|---|---|---|---|---|---|
| 0.18 | 0.341 | 0.129 | 1.818 | 22.74 | 1.397 |
| 0.37 | 0.575 | 0.251 | 1.520 | 24.98 | 1.130 |
| 0.73 | 0.932 | 0.478 | 1.200 | 26.57 | 0.990 |
| 1.46 | 1.471 | 0.885 | 0.898 | 27.02 | 0.957 |
| 2.75 | 2.199 | 1.509 | 0.658 | 26.34 | 0.996 |
| 3.66 | 2.643 | 1.912 | 0.563 | 25.97 | 1.013 |
| 5.49 | 3.436 | 2.655 | 0.446 | 25.62 | 1.021 |
| 9.15 | 4.827 | 3.996 | 0.324 | 25.29 | 1.024 |
| 12.81 | 6.088 | 5.232 | 0.259 | 25.01 | 1.033 |
| 16.47 | 7.277 | 6.404 | 0.218 | 24.68 | 1.051 |

When practically implementing these principles in a specific x-ray inspection system it is necessary to introduce some corrections of algorithm free parameters. These corrections account for difference between real conditions and assumptions that had been made in the mathematical simulation of radiography inspection process. Basically, introduction of such corrections is a procedure of physical model calibration and its mathematical formalization.

APPENDIX 3

Figure 17:
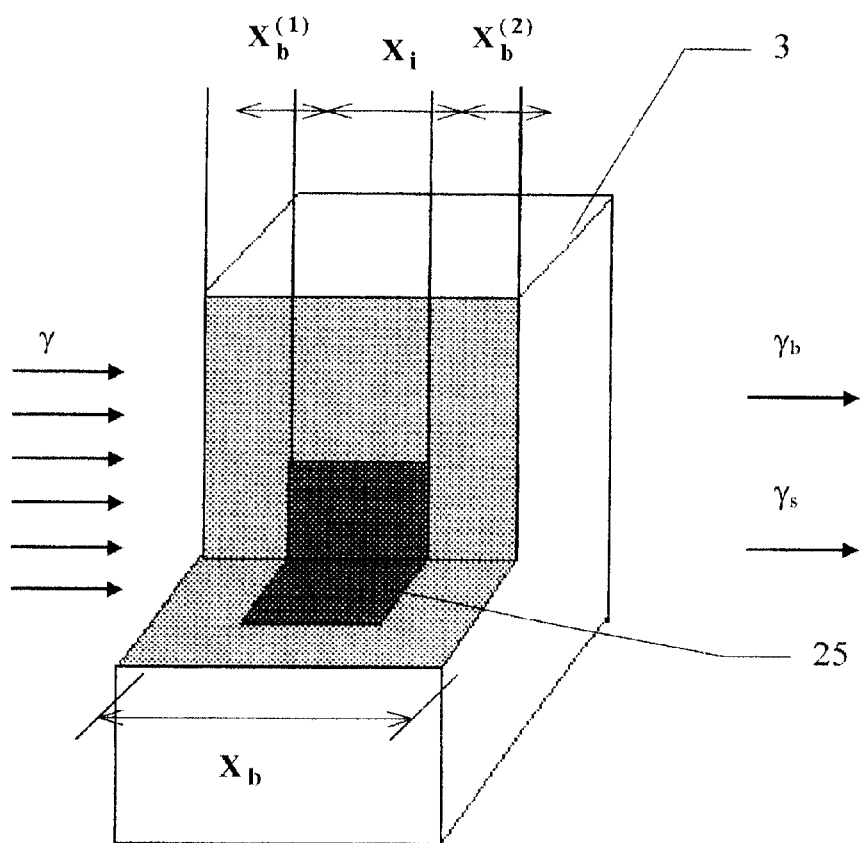

Physical considerations for background subtraction procedure are illustrated in FIG. 17. When quanta of x-ray beams $\gamma_V$ and $\gamma_H$ pass through the inspected object 3 they are partially absorbed by it. Detectors 8 and 12 register quanta that are not absorbed or scattered. Index $\gamma_s$ in FIG. 17 conditionally denotes intensity of x-ray radiation that has passed through the material in front of volume 25, material of volume 25, and material behind volume 25., Index $\gamma_b$ denotes intensity of x-ray radiation that has passed through contents of the inspected object 3 bypassing the area with the suspicious volume 25.

It can be assumed that in reality suspicious volume 25 will be freely placed between walls of the inspected object 3 or inserted into the background contents, e.g. into clothing, causing tighter packing of the background items. In both cases background mass thickness in the direction indicated by the arrow with index $\gamma_s$ will be equal to the background mass thickness along the direction indicated by the arrow with index $\gamma_b$. Mathematically this assumption can be expressed as:

$$X_b = X_b^{(1)} + X_b^{(2)}, \quad (A3.1)$$

here $X_b$ is the cumulative background mass thickness outside the suspicious volume 25 location;

$X_b^{(1)}$ is background mass thickness before the suspicious volume 25;

$X_b^{(2)}$ is background mass thickness behind the suspicious volume 25.

Based on the above considerations and formula (A4.1) mass thickness of the suspicious volume 25 is determined as follows:

$$X_{Vi} = X_{Vs} - X_{Vb} \text{—in vertical projection}; \quad (A3.2)$$

$$X_{Hi} = X_{Hs} - X_{Hb} \text{—in horizontal projection}. \quad (A3.3)$$

EXPLANATION OF ABBREVIATIONS $M_V$ ordinal number of interrogation of multi-channel radiation detector in the first projection $M_H$ ordinal number of interrogation of multi-channel radiation detector in the second projection $N_V$ ordinal number of the elementary detector in the multi-channel radiation detector in the first projection $N_H$ ordinal number of the elementary detector in the multi-channel radiation detector in the second projection $U_1$ normalized response of the elementary detector in the first energy model $U_2$ normalized response of the elementary detector in the second energy model $U_1(M_V, N_V)$ two-dimensional array of normalized responses of elementary radiation detectors of the first projection in the first spectral mode $U_2(M_V, N_V)$ two-dimensional array of normalized responses of elementary radiation detectors of the first projection in the second spectral mode $U_1(M_H, N_H)$ two-dimensional array of normalized responses of elementary radiation detectors of the second projection in the first spectral mode $U_2(M_H, N_H)$ two-dimensional array of normalized responses of elementary radiation detectors of the second projection in the second spectral mode Z effective atomic number of the substance X,g/sq.cm mass thickness of the substance in the direction of x-ray beam $FZ(U_1, U_2)$ analytical approximation of the dependence of Z from $U_1$ and $U_2$ in a specific dual spectra mode in a specific radiographic device $FX(U_1, U_2)$ analytical approximation of the dependence of x from $U_1$ and $U_2$ in a specific dual spectra mode in a specific radiographic device $Z(M_V, N_V)$ two-dimensional array of effective atomic number values in the first projection $X(M_V, N_V)$ two-dimensional array of mass thickness values in the first projection $Z(M_H, N_H)$ two-dimensional array of effective atomic number values in the second projection $X(M_H, N_H)$ two-dimensional array of mass thickness values in the second projection $B(U_1, U_2)$ dependence of video monitor screen gray glow brightness on the value of normalized signal in each spectral mode $C(Z)$ dependence of coloring on the video monitor screen on the effective atomic number $B(M_V, N_V)$ shadow image in the first projection $C(M_V, N_V)$ Z-image in the first projection $B(M_H, N_H)$ shadow image in the second projection $C(M_H, N_H)$ Z-image in the second projection $N_{1V}, N_{2V}$ image boundaries of the rectangular fragment of the potential threat in the first projection $N_{mV}$ coordinate of the center of the potential threat in the first projection $N_{1H}$, $N_{2H}$ image boundaries of the rectangular fragment of the potential threat in the second projection $N_{mH}$ coordinate of the center of the potential threat in the second projection $N_{1V}$, $N_{2V}$, $M_{1V}$, $M_{2V}$ set of four numbers that characterize the coordinates of the rectangular fragment in the image of the potential threat in the first projection $N_{1H}$, $N_{2H}$, $M_{1H}$, $M_{2H}$ set of four numbers that characterize the coordinates of the rectangular fragment in the image of the potential threat in the second projection $N_{1Vb}$, $N_{2Vb}$, $M_{1Vb}$, $M_{2Vb}$ set of four numbers that characterize the coordinates of the rectangular fragment of the background in the first projection $N_{1Hb}$, $N_{2Hb}$, $M_{1Hb}$, $M_{2Hb}$ set of four numbers that characterize the coordinates of the rectangular fragment of the background in the second projection AVERAGE calculation of the average value within the rectangular fragment of video image ERROR calculation of the mean-square error of the value within the rectangular fragment of video image GEOMETRY set of quantitative relationships that bind geometrical coordinates of any point inside the inspection chamber with the coordinate $N_V$ in the first projection and its coordinate $N_H$ in the second projection $Q_V$, $Q_H$ geometrical coordinates of the center of the potential threat inside the inspection chamber $GL_V$ geometrical thickness of the potential threat, which is determined by the location of its fragment boundaries $N_{1V}$ and $N_{2V}$ in the first projection $GL_H$ geometrical thickness of the potential threat, which is determined by the location of its fragment boundaries $N_{1H}$ and $N_{2H}$ in the first projection $R_V$ geometrical thickness of the potential threat along the x-ray beam path in the first projection $R_H$ geometrical thickness of the potential threat along the x-ray beam path in the second projection $Z_{Vs}$ mean effective atomic number of the potential threat fragment in the first projection $\Delta Z_{Vs}$ $Z_{Vs}$ error $X_{Vs}$ mean mass thickness of the potential threat fragment in the first projection $\Delta X_{Vs}$ $X_{Vs}$ error $Z_{Hs}$ mean effective atomic number of the potential threat fragment in the second projection $\Delta Z_{Hs}$ $Z_{Hs}$ error $X_{Hs}$ mean mass thickness of the potential threat fragment in the second projection $\Delta X_{Hs}$ $X_{Hs}$ error $Z_i = \phi(Z_s, X_s, Z_b, X_b)$ analytical expression of the function that approximates dependence of the mean effective atomic number of the potential threat on physical parameters of the fragment, where the potential threat and the background overlap, and physical parameters of the background ("background elimination")

$D_{Vi} = X_{Vi}/R_V$ mean density of the potential threat determined taking into account its mass thickness in the first projection $\Delta D_{Vi}$ $D_{Vi}$ error $D_{Hi} = X_{Hi}/R_H$ mean density of the potential threat determined taking into account its mass thickness in the second projection $\Delta D_{Hi}$ $D_{Hi}$ error AVWEIGHT calculation of weighted average value ERWEIGHT calculation of weighted average value error $Z_1$ weighted average effective atomic number of the potential threat $\Delta Z_1$ $Z_i$ error $D_1$ weighted average density of the potential threat $\Delta D_1$ $D_i$ error BANK(($Z_1 < Z_i < Z_2$; $D_1 < D_i < D_2$); array of two-dimensional (effective atomic number—($Z_3 < Z_i < Z_4$; $D_3 < D_i < D_4$); ...) substance density) ranges of physical parameters that are characteristic for contraband substances or substance groups ($Z_i$, $D_i$) couple of parameters of the potential threat ($\Delta Z_i$, $\Delta D_1$) potential threat physical parameters' couple errors COMPARISON checking whether the couple ($Z_i$, $D_i$) falls into any of the ranges of two-dimensional range array BANK RELIABILITY, % relative reliability of decision

What is claimed is:

1. A process for detecting contraband within a container comprising the steps of:

scanning the container with x-rays along a first plane and obtaining a first sequence of one dimensional transmission intensity measurements from outputs of a plurality of x-ray sensors for a first x-ray intensity spectrum, and obtaining a second sequence for the first plane of one dimensional transmission intensity measurements from outputs of a plurality of x-ray sensors for a second x-ray intensity spectrum;

scanning the container with x-rays along a second plane and obtaining a first sequence of a one dimensional transmission intensity measurements from outputs of a plurality of x-ray sensors for a first x-ray intensity spectrum, and obtaining a second sequence for the second plane of one dimensional transmission intensity measurements from outputs of a plurality of x-ray sensors for a second x-ray intensity spectrum;

using said first plane first intensity spectrum sequence of one dimensional transmission intensity measurements and said first plane second intensity spectrum sequence of one dimensional transmission intensity measurements to calculate a sequence of first plane atomic number values and mass thickness values;

using said second plane first intensity spectrum sequence of one dimensional transmission intensity measurements and said second plane second intensity spectrum sequence of one dimensional transmission intensity measurements to calculate a sequence of second plane atomic number values and mass thickness values;

providing a first plane image by processing at least one of said first or second sequence of one dimensional transmission intensity measurements and providing a second plane image by processing at least one of said second plane first or second sequence of one dimensional transmission intensity measurements;

identifying a suspicious area in at least one of said first plane image or said second plane image;

using the atomic number values and mass thickness values calculated for said suspicious area to calculate an average atomic number value and an average density value for the suspicious area; and, comparing the average atomic number value and average density value for the suspicious area with known atomic number values and density values of actual contraband materials and providing an output indicative of whether the calculated average atomic number value and average density value for the suspicious area fall within those of an actual contraband material.

2. The process of claim 1 further including steps of:

combining said first plane atomic number values with said first plane image to provide a representative first plane atomic number display image thereof; and, combining said second plane atomic number values with said second plane image to provide a representative second plane atomic number display image thereof.

3. The process of claim 2 wherein, during the steps of combining and providing first and second plane atomic number display images, different atomic numbers are displayed in different colors.

4. The process of claim 3 wherein different colors are displayed on said atomic number display images for organic substances, explosives and drugs, light and heavy metals.

5. The process of claim 2 further including a step of identifying a suspicious area wherein an operator views and draws a frame around said suspicious area including a background area on said first plane atomic number display image, and the said operator also views and draws a corresponding frame around said suspicious area including background area on said second plane atomic number display image.

6. The process of claim 5 wherein during the step of identifying said suspicious and background areas the operator views said suspicious and background areas on both said first and second plane atomic number display images, and using a computer mouse clicks about said suspicious and background areas to automate definition thereof.

7. The process of claim 1 wherein during the step of identifying said suspicious area an operator views and draws a frame around said suspicious area including a background area on said first plane image, and also views and draws a frame around said suspicious area including a background area on said second plane image.

8. The process of claim 7 wherein during the step of identifying said suspicious area the operator views said suspicious and background areas of either said first plane image or said second plane image and using a computer mouse clicks about said suspicious and background areas to automate definition thereof.

9. The process of claim 7 wherein prior to the step of calculating the average atomic number value and average density value for the suspicious area, an average mass thickness for the suspicious area in said first plane image is calculated by subtracting a background area mass thickness value from the calculated mass thickness value for said suspicious area thereof, and an average mass thickness for the suspicious area in said second plane image is calculated by subtracting a background mass thickness value from the calculated mass thickness value for said suspicious area thereof.

10. The process of claim 1 wherein a first plurality of x-ray sensors are used during the steps of scanning two different x-ray energy levels to obtain the first and second sequences of one dimensional transmission intensity measurements along said first plane, and a second plurality of x-ray sensors are used during the steps of scanning two different x-ray energy levels to obtain the first and second sequence of one dimensional transmission intensity measurements along said second plane.

11. The process of claim 1 wherein every other x-ray sensor is provided with a filter and wherein said first sequence of one dimensional transmission intensity measurements are obtained from outputs of filtered sensors and said second sequence of one dimensional transmission intensity measurements are obtained from outputs of non-filtered x-ray sensors.

12. The process of claim 1 wherein said first and second sequence of one dimensional transmission intensity measurements of said first plane are combined to provide a first gray scale x-ray image for said first plane, and said first and second sequence of one dimensional transmission intensity measurements of said second plane are combined to provide a second gray scale x-ray image for said second plane.

* * * * *